US009101933B2

(12) United States Patent
Haswell

(10) Patent No.: US 9,101,933 B2
(45) Date of Patent: Aug. 11, 2015

(54) MICROFLUIDIC APPARATUS AND METHOD FOR DNA EXTRACTION, AMPLIFICATION AND ANALYSIS

(75) Inventor: Stephen John Haswell, Humberside (GB)

(73) Assignee: University of Hull (GB)

( * ) Notice: Subject to any disclaimer, the term of this patent is extended or adjusted under 35 U.S.C. 154(b) by 587 days.

(21) Appl. No.: 13/123,524

(22) PCT Filed: Oct. 12, 2009

(86) PCT No.: PCT/GB2009/051360
§ 371 (c)(1),
(2), (4) Date: Jun. 22, 2011

(87) PCT Pub. No.: WO2010/041088
PCT Pub. Date: Apr. 15, 2010

(65) Prior Publication Data
US 2011/0244467 A1 Oct. 6, 2011

(30) Foreign Application Priority Data

Oct. 10, 2008 (GB) .................................. 0818609.0

(51) Int. Cl.
| C12P 19/34 | (2006.01) |
| B01L 3/00 | (2006.01) |
| B01L 7/00 | (2006.01) |
| C12N 15/10 | (2006.01) |
| C12Q 1/68 | (2006.01) |
| G01N 27/447 | (2006.01) |

(52) U.S. Cl.
CPC ....... *B01L 3/50273* (2013.01); *B01L 3/502761* (2013.01); *B01L 7/52* (2013.01); *C12N 15/1003* (2013.01); *C12Q 1/6858* (2013.01); *G01N 27/4473* (2013.01); *B01L 2200/0631* (2013.01); *B01L 2200/10* (2013.01); *B01L 2300/069* (2013.01); *B01L 2300/0627* (2013.01); *B01L 2300/087* (2013.01); *B01L 2300/0816* (2013.01); *B01L 2300/1866* (2013.01); *B01L 2400/0415* (2013.01); *B01L 2400/0421* (2013.01)

(58) Field of Classification Search
CPC ............ C12Q 1/6858; C12Q 2565/629; B01L 2300/87; B01L 2200/10; B01L 2400/0421
USPC ........................................................ 435/91.2
See application file for complete search history.

(56) References Cited

U.S. PATENT DOCUMENTS

| 5,922,591 | A | 7/1999 | Anderson et al. |
| 6,306,590 | B1 | 10/2001 | Mehta et al. |
| 6,852,284 | B1 | 2/2005 | Holl et al. |
| 8,017,340 | B2 | 9/2011 | Collier et al. |
| 2002/0022261 | A1 | 2/2002 | Anderson et al. |
| 2002/0090320 | A1 | 7/2002 | Burow et al. |
| 2003/0087290 | A1 | 5/2003 | Tarlov et al. |
| 2003/0190608 | A1 | 10/2003 | Blackburn |
| 2004/0238355 | A1 | 12/2004 | Kimizuka |
| 2005/0161327 | A1 | 7/2005 | Palmieri |
| 2005/0244882 | A1 | 11/2005 | Gauch et al. |
| 2006/0088929 | A1 | 4/2006 | Nakajima et al. |
| 2007/0172388 | A1 | 7/2007 | Padmanabhan et al. |
| 2007/0254372 | A1 | 11/2007 | Bickel et al. |
| 2008/0003142 | A1 | 1/2008 | Link et al. |
| 2008/0213912 | A1 | 9/2008 | Randall et al. |
| 2011/0124114 | A1 | 5/2011 | Ermantraut et al. |
| 2011/0244467 | A1 | 10/2011 | Haswell |

FOREIGN PATENT DOCUMENTS

| EP | 1 016 864 A2 | 5/2000 |
| EP | 1 063 204 A2 | 6/2000 |
| EP | 1161989 | 12/2001 |
| EP | 1 330 541 A1 | 7/2003 |
| EP | 1 064 090 B1 | 9/2003 |
| EP | 1 007 953 B1 | 6/2006 |
| EP | 0 821 791 B1 | 10/2006 |
| EP | 1806393 | 7/2007 |
| EP | 1 330 541 B1 | 6/2008 |
| EP | 1 086 369 B1 | 12/2008 |
| EP | 1086369 B1 | 12/2008 |
| GB | 2446204 A | 8/2008 |
| JP | 11509094 | 8/1999 |
| JP | 2008525037 | 7/2008 |
| WO | 95/10034 | 4/1995 |
| WO | 96/31522 | 10/1996 |

(Continued)

OTHER PUBLICATIONS

Setterquist et al., Nucleic Acids Research, vol. 24, No. 8, pp. 1580-1581, 1996.*
International Search Report for PCT/GB2009/051360, Completed by the European Patent Office on Mar. 22, 2010, 3 Pages.
Search Report for GB 1015803.8, Date of Search Jan. 25, 2011, 1 Page.
Belgrader et al. "A Battery-Powered Notebook Thermal Cycler for Rapid Multiplex Real-Time PCR Analysis", Anal. Chem. 2001, vol. 73, p. 286-289.
Lagally et al. "Monolithic integrated microfluidic DNA amplification and capillary electrophoresis analysis system", Sensors and Actuators B 2000 vol. 63, p. 138-146.

(Continued)

*Primary Examiner* — Cynthia B Wilder
(74) *Attorney, Agent, or Firm* — Brooks Kushman P.C.

(57) ABSTRACT

An integrated gel based microfluidic sample processing device, suitable for forensic investigations at the scene of a crime, including a substrate having a plurality of micro-channels to form at least a DNA extraction chamber in fluidic cooperation with an amplification chamber which in turn is in fluidic cooperation with a separation and detection channel. The micro-channels containing a DNA extraction material and gel based reaction reagents necessary for processing the sample. The device further having electrical contacts for coupling to an external power source and capable of inducing electro-kinetic manipulation of the gel based reagents and DNA extracted from the sample throughout the device.

15 Claims, 13 Drawing Sheets

(56) References Cited

FOREIGN PATENT DOCUMENTS

| | | |
|---|---|---|
| WO | 96/36737 | 11/1996 |
| WO | 96/42013 | 12/1996 |
| WO | 9702357 | 1/1997 |
| WO | 99/09042 | 2/1999 |
| WO | 99/19056 | 4/1999 |
| WO | 9960397 | 11/1999 |
| WO | 9964848 A1 | 12/1999 |
| WO | 00/46595 | 8/2000 |
| WO | 01/25138 A1 | 4/2001 |
| WO | 01/40520 A1 | 6/2001 |
| WO | 01/86249 A2 | 11/2001 |
| WO | 02/064253 A2 | 8/2002 |
| WO | 02/070118 A2 | 9/2002 |
| WO | 02/081729 A2 | 10/2002 |
| WO | 03/042677 A1 | 5/2003 |
| WO | 03/092893 A1 | 11/2003 |
| WO | 2004/039499 A2 | 5/2004 |
| WO | 2005032717 | 4/2005 |
| WO | 2005/066372 A2 | 7/2005 |
| WO | 2005097969 | 10/2005 |
| WO | 2006/029387 A1 | 3/2006 |
| WO | 2006046433 | 5/2006 |
| WO | 2006071770 | 7/2006 |
| WO | 2006/093865 A1 | 9/2006 |
| WO | 2007032788 | 3/2007 |
| WO | 2007/047336 A2 | 4/2007 |
| WO | 2007/061943 A2 | 5/2007 |
| WO | 2007/120248 A2 | 10/2007 |
| WO | 2007133710 A2 | 11/2007 |
| WO | 2007140015 A2 | 12/2007 |
| WO | 2008/052138 A2 | 5/2008 |
| WO | 2008/124064 A1 | 10/2008 |
| WO | 2009/021240 A2 | 2/2009 |
| WO | 2009016652 | 2/2009 |
| WO | 2009021240 A2 | 2/2009 |
| WO | 2009/048878 A2 | 4/2009 |
| WO | 2009/094164 A1 | 7/2009 |
| WO | 2009112594 | 9/2009 |
| WO | 2009153189 | 12/2009 |
| WO | 2010041088 | 4/2010 |
| WO | 2010101708 A2 | 9/2010 |

OTHER PUBLICATIONS

Oakley et al. "Development of a Bi-functional silica monolith for electro-osmotic pumping and DNA clean-up/ extraction using gel-supported reagents in a microfluidic device", Lab Chip. 2009, vol. 9, p. 1596-1600.

Malic et al. "Current State of Intellectual Property in Microfluidic Necleic Acid Analysis", Recent Patents on Engineering 2007, vol. 1, p. 71-88.

Seed. "Silanizing Glassware", Current Protocols in Immunology 1997, Supplement 21, p. A.3K.1-A.3.K2.

Search Report for GB 0818609.0, Date of Search Feb. 9, 2009, 4 Pages.

Shaw et al. Lab Chip 2010, 8 pages, "Rapid PCR amplication using a microfludic device with integrated microwave heating and air impingement cooling."

* cited by examiner

MICROFLUIDIC APPARATUS AND METHOD FOR DNA EXTRACTION, AMPLIFICATION AND ANALYSIS

CROSS-REFERENCE TO RELATED APPLICATION

This application is the U.S. national phase of PCT Appln. No. PCT/GB2009/051360 filed Oct. 12, 2009 which claims priority to Great Britain application 0818609.0 filed Oct. 10, 2008, the disclosures of which are incorporated in their entirety by reference herein.

FIELD OF INVENTION

The present invention relates to a microfluidic sample processing device, methods and system. More particularly, the present invention relates to a microfluidic sample processing device with micro-channels having gel supported samples and reagents, and a fully integrated, portable DNA analyser using same.

State of the art microfluidic devices, also sometimes known as "Lab-on-chip" or "micro-total analysis systems" generally comprise a substrate and microstructures such as micro-channels and ports. The use of such microfluidic devices allows the use of dedicated micro-channels which feature multiple layers of materials such as silicon, glass and polymer thus allowing miniaturisation of normal sized equipment such that it can be readily portable.

Compared to devices of the same type in normal size, such microfluidic devices have various advantages including the fact that only very small amounts of samples and reagents are required, the analysis time required is shorter and the sensitivity of the test carried out therein is higher than in their normal sized counterparts. In addition reduction in potential contamination and greater portability to a site for on-site analysis is more readily possible.

Traditionally methods such as DNA fingerprinting takes about a day or in some cases as much as a week and the use of a number of different devices to complete the procedure. It is therefore difficult to make a quick shortlist of, for example crime suspects, using DNA soon after a crime has occurred. However, a variety of operations exist such as chemical reactions, synthesis, purification, extraction, generation and/or analysis which can be performed in such prior art microfluidic devices. They can therefore find wide application in many analytical and diagnostic fields such as DNA fingerprinting, gene analysis, clinical diagnosis, drug screening, and environmental monitoring.

The fabrication methodology associated with microfluidic devices offer an attractive route to developing novel research tools as they introduce the possibility of integrating different processes onto one device, which in turn can lead to automated systems which increase the robustness of an analytical measurement. However in some cases integration has proved difficult to implement due to the high degree of complexity associated with successfully transporting a discrete volume of sample from one area of the device to another without the requirement to couple the device to auxiliary equipment such as pumps.

State of the art microfluidic devices or systems in which they are utilised usually all require external hydrodynamic pumping, with the exception of electrophoretic separation, which is potentially a very inefficient method of manipulating microliters of fluid as it requires excessive dead volumes. Furthermore, the prior art devices generally comprise solution based technology and thus it is difficult to prepare and store reagents within a microfluidic device in a manner that will offer stable electro-kinetic control of a sample especially if, for example, air bubbles enter the system or a solution dries.

In particular, practical devices that combine on a single chip modules for DNA extraction and purification from tissue, DNA amplification, sample separation and detection with a practical transport mechanism such that the steps may be performed in successive manner by components in microfluidic communication have proved difficult to fabricate and operate effectively. Effective and consistent localisation of the different reagents, effective provision of an interface for receiving a real world lysed tissue sample, and an efficient transport mechanism to transport the extracted sample consistently through the chip has particular difficulties.

For example, WO 99/64848 describes a partly integrated microfluidic device. Movement is carried out by electrokinetic mobility (electroosmotic) in liquids and features an electrokinetic injection into a gel where electrophoretic separation is carried out. Detection is by fluorescence and is based on sequencing applications. However, DNA extraction and purification is still carried out off chip.

US2003/190608 describes a system in which a bead with a complimentary DNA/RNA sequence is held in a gel through which a sample is pumped hydrodynamically. A hybridisation process which includes thermal amplification is described but reagents are added via a reservoir using a pump rather than localized within the device. Fluorescence detection is carried out on chip but no separation is described or required for this particular application. Additionally, DNA extraction is again carried out off chip.

US2005/161327 is a device based on dielectrophoresis pumping rather than electrokinetic. The sample preparation is off device as is reagent addition and the entire process is solution based. No separation process is described.

WO2007/133710 describes plug or droplet based solution processing and focuses mainly on droplet manipulation processes such as mixing and splitting. Reagents are not held on the device.

One of the main issues associated with integration of extraction, amplification and separation and detection within a single device is that integration compromises the known operating conditions for the individual processes. Re-optimisation of the operating conditions is difficult to achieve as the system must operate as a standalone complex process in which the interaction between the individual processes are harmonised.

For these reasons and others, effective microfluidic devices that perform extraction and purification, amplification, sample separation and detection on a single chip have proved elusive.

SUMMARY OF INVENTION

According to the present invention there is provided an integrated gel based microfluidic sample processing device comprising a substrate having a plurality of micro-channels to form at least a DNA extraction chamber in fluidic cooperation with an amplification chamber which in turn is in fluidic cooperation with a separation and detection channel; said micro-channels containing a DNA extraction material and gel-based reagents necessary for processing said sample; the device further comprising electrical contacts for coupling to an external power source and capable of inducing electrokinetic manipulation of said gel based reagents and DNA extracted from said sample throughout the device.

By the term "gel based reagents" it is meant that the reagents required to purify and elute an extracted DNA sample and support the PCR reaction are supported in a gel matrix within the microfluidic device.

The substrate for the microfluidic device is preferably formed of inert electrically non-conductive, preferably optically transparent, material such as glass or other similar substance or material. The substrate is generally sealed for use by a lid to enclose the internal micro-channels defined therein. The lid can be attached or bonded by any suitable means to the substrate.

The device may be of a size dictated by the analyser into which it is to be placed. Alternatively the size is in the region of 120 mm by 60 mm but other sizes of up to 120 mm or more by up to 60 mm or more may also be suitable. A device of small dimensions is preferred so that the device is suitable for use in a portable system. Furthermore, such a device can be easily fabricated.

The DNA extraction chamber may comprise a means for introduction thereinto of a lysed sample, for example comprising an inlet port. Conveniently this comprises or is in fluid communication with a sample receiving means. A sample receiving means may be adapted to provide for introduction of a lysed sample directly into the DNA extraction chamber. In a preferred embodiment, the sample may be received thereinto comprising DNA material in admixture with a lysis agent. Accordingly, the sample receiving means may be adapted to provide for reception of an unlysed tissue sample, lysis thereof, and introduction of the lysed sample into the DNA extraction chamber. For example, a sample receiving means may comprise an absorbent member for receiving a tissue sample in use, pre-loaded with a lysis agent, and adapted in use to be placed in fluid communication with a DNA extraction chamber introduction port to receive, lyse and introduce the lysed sample thereinto, when so placed. A suitable lysis agent is a chaotropic salt solution. A suitable chaotropic salt is guanidine hydrochloride, as in addition to lysis of the tissue sample, such a salt facilitates subsequent binding of the DNA to the DNA extraction material (as discussed below) and inactivates deoxyribonucleases (DNases) which would otherwise go on to enzymatically digest the extracted DNA.

The DNA extraction material may be capable of trapping DNA, allowing the remaining volume of the lysed sample to pass through the material or it may be capable of trapping the main volume of the lysed sample, allowing DNA to pass through the material. Preferably the DNA extraction material is charged to allow trapping of DNA therein and is located in the DNA extraction chamber. More preferably, the DNA extraction material is a porous solid-phase extraction material. Solid-phase extraction (SPE) enables the pre-concentration of a sample and the removal of potential contaminants that may interfere with downstream applications such as the polymerase chain reaction (PCR). In addition, SPE also allows pre-concentration of the DNA, important when dealing with limited samples.

More preferably yet, the DNA extraction material is a silica based extraction material and for example a silica bead or more preferably a silica based monolith. A silica based extraction material, such as a silica based monolith, is preferred as it not only extracts DNA from the lysed sample but also acts as a pump for electroosmotic flow (EOF), thereby increasing the efficiency of the extraction step, as discussed in further detail below.

Where the DNA extraction material is negatively charged, as in a silica based monolith, the presence of a chaotropic agent, such as a chaotropic salt solution, either as the lysis agent where lysis is carried out on the chip or preloaded into the relevant channel(s) of the device where lysis is carried out off chip, facilitates binding of the DNA present in the lysed sample to the DNA extraction material. This is because the chaotropic agent has a high ionic strength and so is capable of reducing the negative potential at the surface of the extraction material. This allows dehydration of the DNA and extraction material surfaces and formation of intramolecular hydrogen bonds within the DNA/extraction material contact layer to become dominant, thereby enhancing binding of DNA to the extraction material. Furthermore, the chaotropic agent forms hydrated ions by sequestering water molecules, reducing the solvation of DNA and the extraction material surface. Additionally, the chaotropic agent denatures the DNA allowing the exposed bases of the single-stranded (ss) DNA molecules to hydrogen bond with the surface of the extraction material.

In a preferred embodiment of the present invention, where lysis of the tissue sample is performed on the device, the lysis agent may further comprise a carrier molecule such as ribonucleic acid (RNA). Use of such a carrier RNA has a more pronounced effect on increasing DNA extraction efficiency, particularly when lower amounts of DNA are present in the sample. It is believed that on an extraction material, such as a silica based monolith, there are always a certain number of sites which will irreversibly bind nucleic acids. By including carrier RNA in the lysis agent, it can sacrificially bind to these sites to minimise loss of important DNA, leading to greater recoveries.

The silica based monolith is preferably thermally activated or photoinitiated. Thermal activation of the silica monolith is preferable over photoinitiation as it provides particular advantages such as ease of use, speed of production, reproducibility and precision localisation on fabricated microfluidic devices. The monolith is generally porous and capable of accepting a lysed sample via an introduction port within or adjacent thereto.

It is preferred that the DNA extraction chamber also comprises a wash inlet port and wash outlet port in fluidic connection therewith. In a preferred embodiment, the DNA extraction chamber further comprises a channel containing an elution reagent supported in a gel capable of eluting the DNA from the DNA extraction material once it has been washed. Preferably the elution gel contains a low ionic strength buffer, for example water.

The device also comprises a plurality of further channels, inlet and outlet ports which are provided for the introduction or movement around the device or removal of reagents or waste.

Preferably the gel based reagents in each of the at least one DNA extraction chamber, amplification chamber and separation and detection channel relate to the nature of the process taking place therein. Such gel based reagents can, if desired, be selected for their ability to form a matrix when in situ in the device. Known gels suitable for gel based electrophoresis, and in particular for their ability to form a matrix when in situ in the device, include those based on linear polysaccharides. The gel preferably comprises at least one linear polysaccharide, which linear polysaccharide may optionally be admixed with other linear polysaccharides and/or at least one non-linear polysaccharide. Agarose-based gels are particularly suitable. The at least one linear polysaccharide therefore preferably comprises agarose, and agarose may, in some embodiments, be the predominant or only gel forming material present.

Preferred gels for use in electrophoretic separation may be based on polyethylene oxide (PEO) or linear polyacrylamide (LPA). The degree of polymer present in such gels allows controlled flow to be achieved such that the gel is localised in the separation channel following injection thereinto. Preferably, the degree of polymer is from 3 wt % to 7 wt % of the separation gel media as these levels of polymer are capable of forming a polymer matrix to impart retardation of the PCR amplification products and allow successful separation.

The use of gel based reagents thus enables fixing of the different process reagents with precision localisation on the fabricated microfluidic device according to the invention. All of the stages, DNA extraction from the lysed sample, DNA amplification, for example using the polymerase chain reaction (PCR), separation and detection, may be performed in successive localised manner by components in microfluidic communication on a microfluidic device in accordance with the invention. In particular, the extraction chamber, by extracting DNA from a lysed sample, provides a much more effective real world interface for a microfluidic device in which all the stages of extraction, amplification, separation and detection may be performed in successive localised manner on a single device.

The gel based reagents may also contain optical probes that can attach to selected DNA fragments so they can be detected during the separation process. The optical probes may be capable of reflecting or absorbing light shone on the DNA fragments to which they are attached or they may be capable of emitting light. Preferably, the optical probes are fluorescent dyes or chemiluminescent dyes. More preferably the optical probes are fluorescent dyes which attached to the 5' end of the DNA fragments and become incorporated into the PCR products during amplification. Suitable probes include one or more of the following fluorescent dyes: 5-carboxyfluorescein (FAM), 5'-dichloro-dimethoxy-fluorescein (JOE), tetramethylrhodamine (TAMRA) and carboxy-X-rhodamine (ROX).

Separation as used herein should accordingly be interpreted broadly as encompassing all mechanisms by which DNA fragments of the amplified product can be selectively distinguished for detection, including optical separation for example via optoluminescent techniques such as those using fluorescent dyes or chemiluminescent dyes, whether or not supplemented by spatial and/or temporal physical separation of the DNA fragments and/or plural separation of DNA fragments for use with multiple reagents in parallel. Such optical separation occurs because the fluorescent dyes employed emit at different characteristic wavelengths. Therefore, even where the fluorescent dyes are present simultaneously, i.e. in the same position in the separation and detection channel, standard spectrometers can distinguish the individual probes present and so detect the profile of the DNA sample introduced into the device.

The device comprises a plurality of electrodes to electrokinetically manipulate the gel based reagents and the DNA extracted from the sample and the PCR products throughout the device; said electrodes are sealably connected to the device by one end, the other being connectable to a power source. The term electro-kinetically includes electrophoresis, electroosmotic flow, and any other means of electrically manipulation which will be apparent to one skilled in the art. In a preferred mode of operation, the extracted DNA is manipulated through subsequent stages until it reaches the amplification chamber by electroosmosis. Thereafter electrophoresis is generally preferred.

According to a further aspect of the invention there is provided a portable, integrated system for analysis of DNA in a biological sample comprising an electrokinetically driven system for extraction, purification, amplification, separation and analysis of DNA fragments generated from said sample, said system further comprising a gel based microfluidic sample processing device comprising a substrate having a plurality of micro-channels to form at least a DNA extraction chamber in fluidic cooperation with an amplification chamber which in turn is in fluidic cooperation with a separation and detection channel, a plurality of electrodes positioned within the microfluidic device and coupled to a power source are configured to electro-kinetically manipulate the gel based reagents and DNA and DNA fragments around the microfluidic device, wherein the microfluidic device is adapted to receive the sample via the DNA extraction chamber; the system also comprises a heating element coupled or adjacent to the microfluidic sample processing device;

a detector positioned to detect DNA fragments by a detectable signal; and a portable housing configured to contain the microfluidic device, electrokinetically driven system, the detector and the power source.

The heating element may comprise any suitable means for achieving thermal cycling of the DNA fragments and may include a specific cooling element. A heating element might be a contact or non-contact heating element. Commonly used contact heating elements include block heaters, e.g. Peltier heaters, or the deposition of thin film resistive heaters, e.g. platinum, on the exterior of the microfluidic device. While Peltier heaters are widely used to achieve thermal cycling for DNA amplification as they produce reliable heating, they suffer from relatively slow temperature ramp rates. Non-contact heating methods described for DNA amplification in microfluidic systems include the use of infrared and halogen lamps, induction heating and alternating electric current induced joule heating. In a preferred case the heating element comprises a source of microwave radiation.

The integrated system of this aspect of the invention typically makes use of the microfluidic sample processing device of the first aspect of the invention, and preferred features of the system will be understood by analogy.

In a yet further aspect of the invention there is provided a method of DNA analysis comprising:

a) introducing a sample into a DNA extraction chamber of a gel based microfluidic sample processing device located in an analyser system;

b) performing electro-kinetic manipulation of the sample within the DNA extraction chamber to wash and purify DNA;

c) eluting the DNA in the DNA extraction chamber to an amplification chamber;

d) amplifying the DNA fragments in the amplification chamber to form an amplification product (DNA fragments) within a gel;

e) electro-kinetically injecting said amplification product into a separation channel; and f) performing electro-kinetic separation of said amplification product to form a DNA profile.

Preferably, the sample is lysed prior to being introduced into the DNA extraction chamber of the device.

In one embodiment of the method, the sample is lysed prior to being introduced into the device. The lysed sample may be introduced comprising DNA in admixture with a chaotropic salt, e.g. as solution. For example, the lysed sample in a chaotropic salt solution is manually loaded onto an extraction material structure such as a silica monolith orthogonal to the subsequent flow of wash and elution solutions.

In another embodiment of the method, a sample lysis step is performed at or on the device. For example, the sample may be introduced by the following steps:
providing an absorbent member loaded with a lysis agent;
applying an unlysed biological sample onto the absorbent member;
applying and/or retaining the absorbent member at a sample receiving site in fluid communication with the DNA extraction chamber to introduce lysed sample thereinto.

The DNA extraction chamber contains a DNA extraction material. Extraction and elution of the DNA may be performed in one step when the DNA extraction material is capable of trapping the remaining volume of the lysed sample, allowing the DNA fragments to pass through the material. Alternatively, if the DNA extraction material is capable of trapping the DNA fragments, elution of the DNA fragments will be performed in a separate step to the extraction.

Preferred features of the DNA extraction material are set out hereinabove. In particular, the DNA extraction material is preferably charged. More preferably the DNA extraction material is a solid-phase extraction material. More preferably yet the DNA extraction material is a silica based extraction material and, for example, comprises at least one silica bead or more preferably a silica based monolith.

The lysed sample may be washed by electro-kinetically manipulating a reagent from a wash inlet to a wash outlet of the DNA extraction chamber. In a preferred embodiment of the present invention, electro-kinetic manipulation of the wash reagent within the DNA extraction chamber of the device is performed by electroosmotic manipulation.

As stated previously, the use of a silica-based extraction material is preferable as it can act as a pump for electroosmotic flow (EOF), thereby enhancing extraction and wash step of DNA from the lysed sample. This is true of any negatively charged extraction material and occurs as a result of the greater surface area of the silica-based extraction material compared to, for example, the surface area of the channel only. EOF is a surface effect and so the increased surface area provides increased pump support. Furthermore, such an extraction material acts as a one-way valve restricting hydrodynamic backflow of the sample due to hydrodynamic resistance which results from the presence of small pores within the material which have high capillary resistance to hydrodynamic pressure flow. The prevention of backflow is very important as without backflow control, the movement of the sample quickly stops as the backflow, due to the hydrodynamic pressure difference, quickly balances out the forward EOF.

In a preferred embodiment of the invention, elution of the DNA in the DNA extraction chamber to the amplification chamber is performed by electro-kinetic manipulation.

Electroosmotic manipulation is preferred in steps b) and c) as it will effect bulk movement of the sample through the gel and DNA extraction material in order to extract DNA from the lysed sample and transfer the DNA to the amplification chamber.

The method of this aspect of the invention typically makes use of the microfluidic sample processing device or integrated system of the first or second aspect of the invention, and preferred features of the system will be understood by analogy.

Preferably amplification of DNA extracted from the sample to form the DNA fragments is performed via Polymerase Chain Reaction (PCR).

The electro-kinetic injection and separation of the amplification product to form a DNA profile may be performed by electrophoresis. Electrophoretic separation is a preferred method as it involves displacement of ions in an electrical field, thereby effecting separation of the DNA fragments (typically based on size of the fragments) to create a DNA profile.

The method can additionally include the step of detecting the DNA profile produced by the electro-kinetic separation. Detection signals generated by detecting the DNA profile can then be transferred to output means such that the profile can be viewed graphically. Additionally the method may comprise the step of comparing the profile produced with known profiles such as those held on DNA databases held within the UK National Forensics Science Service or equivalent databases.

Although the present invention is intended to have particular application in the field of forensics, for example, for use on site at scenes of crime, other applications are also envisaged such as determination of genetic traits associated with food authenticity, paternity cases, bacterial/viral infection and strain identification and DNA based security marking.

A fully integrated, portable DNA analyser according to the present invention allows the processing of a DNA sample taken at, for example, "the scene of crime" to be DNA fingerprinted on site within approximately one hour and with reduced or no contamination issues. Such is possible through its streamlining of the diagnostic and analytical process. The speed of the diagnostic and analytical process also makes such devices suitable for use in many other situations where "on-site analysis" is key, such as in custody suites and in airport security facilities. In particular DNA analysis using such an analyser is successful because cell collection is external to microfluidic device, whilst the DNA extraction, amplification of the DNA fragments and separation of the amplified product, and in the optional case also at least part of the sample lysis stage, are all carried out in the microfluidic device.

The specific compact nature of the analyser system allows coordination between each process step and greatly expedites the amplification procedure where DNA fragments are alternatively heated and cooled. As a result, the integrated analyser system can complete the entire process, from DNA extraction to analysis (i.e. genetic profiling) in approximately 1 hour.

The DNA analyser system of the present invention utilises a gel based microfluidic sample processing device and thus utilises electro-kinetic fluidic movement of reagents, DNA and PCR products within the microfluidic device to achieve the DNA analysis. Additionally the incorporation of supported materials by way of a DNA extraction material and gel-based reagents in the gel based microfluidic sample processing provide superior results to those prior art devices on the market which use reagents and samples only in a liquid/solution phase.

The formation of a gel or gel matrix in the microfluidic device is capable of supporting reagents therein over prolonged periods and offers more stable electro-kinetic control of a lysed sample and DNA and amplified DNA fragments, even when bubbles may be present in the system.

Additionally such a device allows introduction of a lysed sample to the device which then undergoes multiple processing by means of successive extraction and/or purification, amplification, and separation within the device, such processing being achieved primarily by electro-kinetic manipulation of the lysed sample and/or DNA through successive interactions with the gel based reagents therein. This is in contrast with prior art devices which are more or less "single step" devices.

Although the present invention has been described in terms of analysing DNA fragments in a biological sample, the skilled person would understand that the invention may equally be applied to the analysis of any nucleic acid material, for example RNA, wherein the process will involve reverse transcription to form DNA suitable for use in PCR. Accordingly, the method may involve performing reverse transcription, and the apparatus may accordingly comprise suitable reagents to perform this step.

Embodiments of the present invention will now be described, by way of example only, with reference to the accompanying figures in which.

Figure 7:
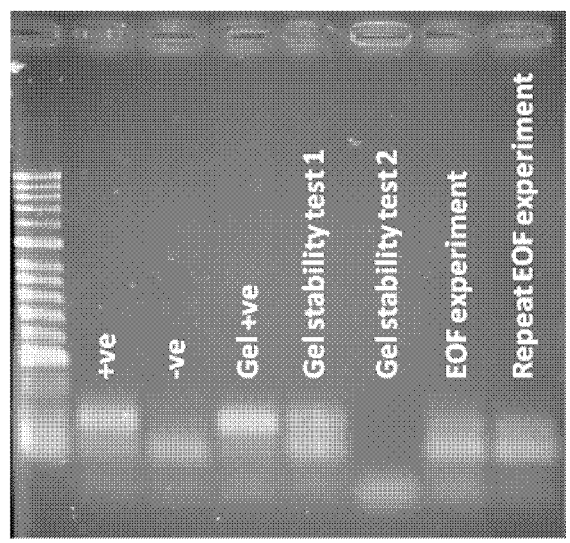

FIG. 7 shows a UV transilluminator image of PCR products obtained by the methodology of the present invention and particularly through the electro-kinetic movement of DNA into PCR reagents in which stability test 1 consisted of gel left at room temperature for 30 minutes and stability test 2 consisted of gel left at room temperature for 1 hour.

Figure 8A:
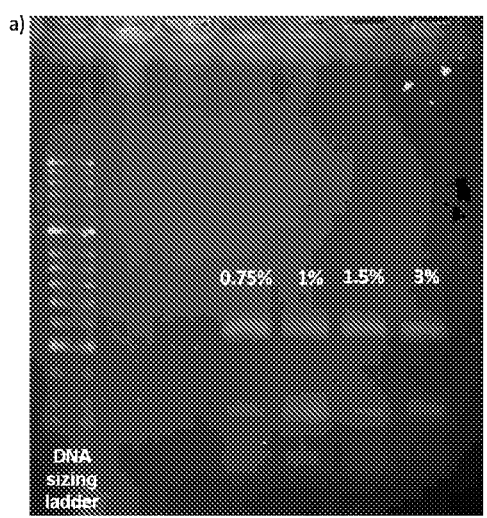
Figure 8B:
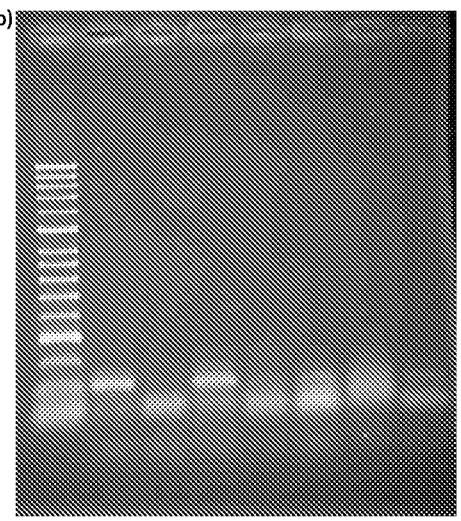
Figure 9:
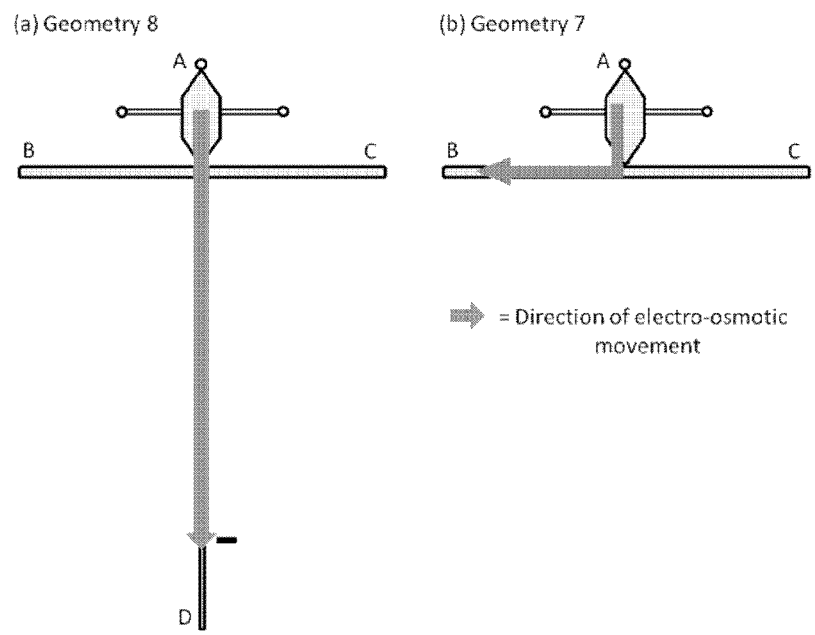
Figure 10:
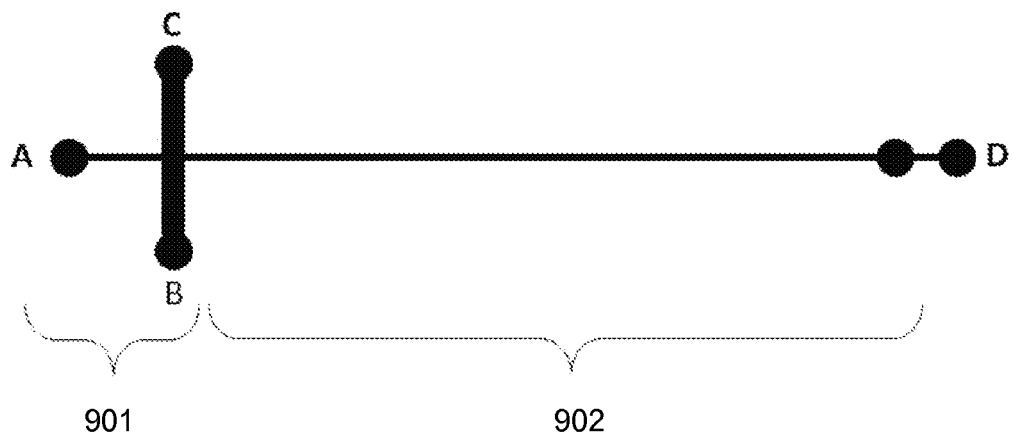
Figure 11:
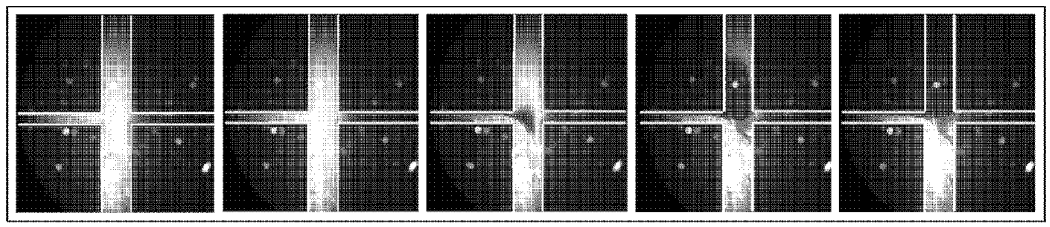
Figure 12A:
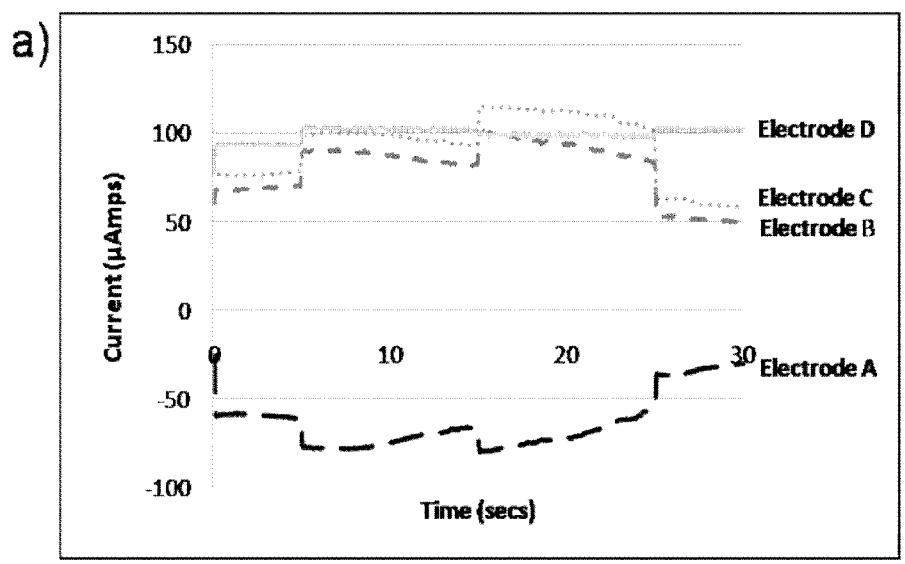
Figure 12B:
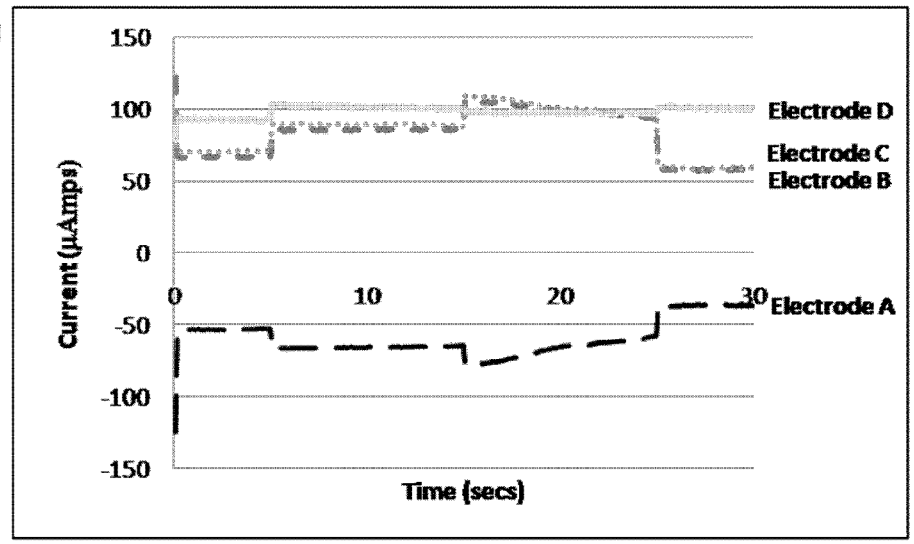
Figure 13:
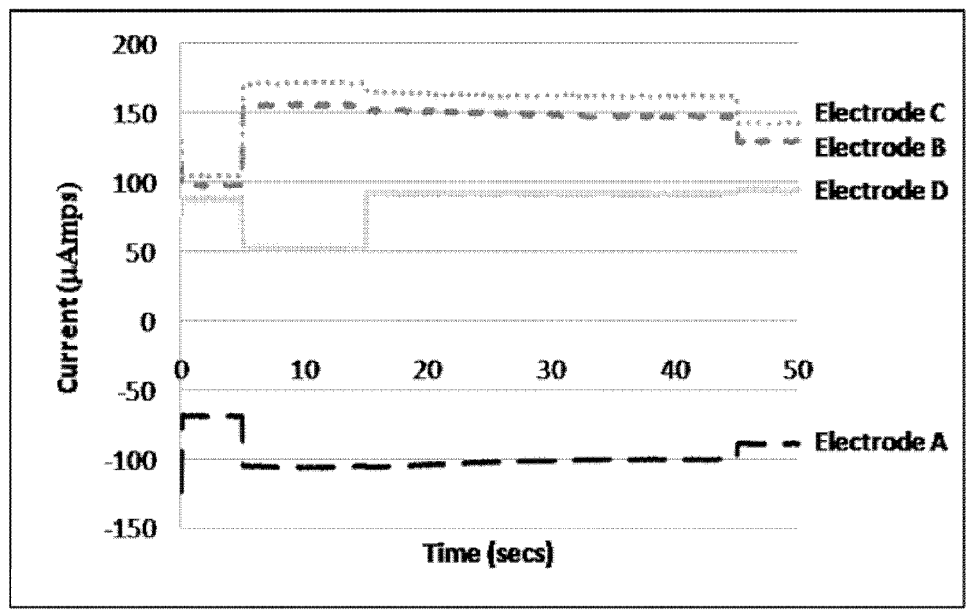
Figure 15:
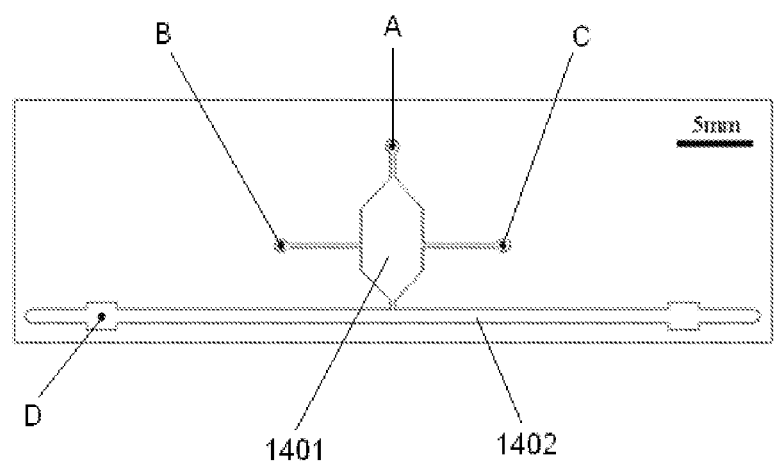
Figure 16:
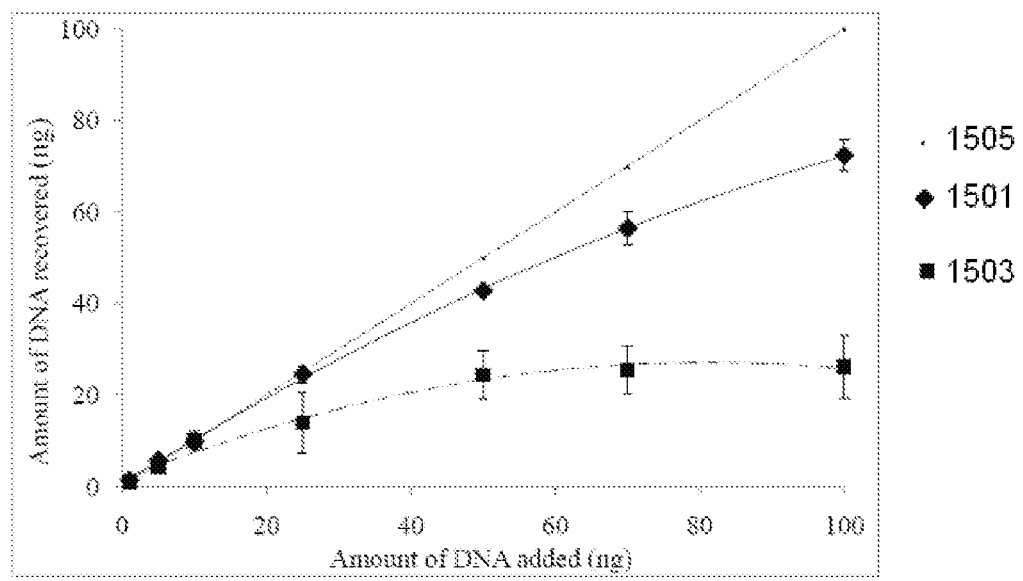
Figure 17A:
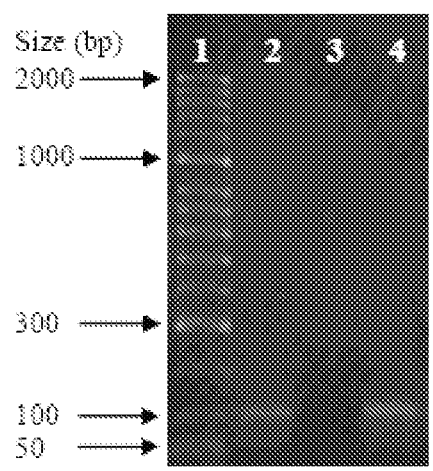
Figure 17B:
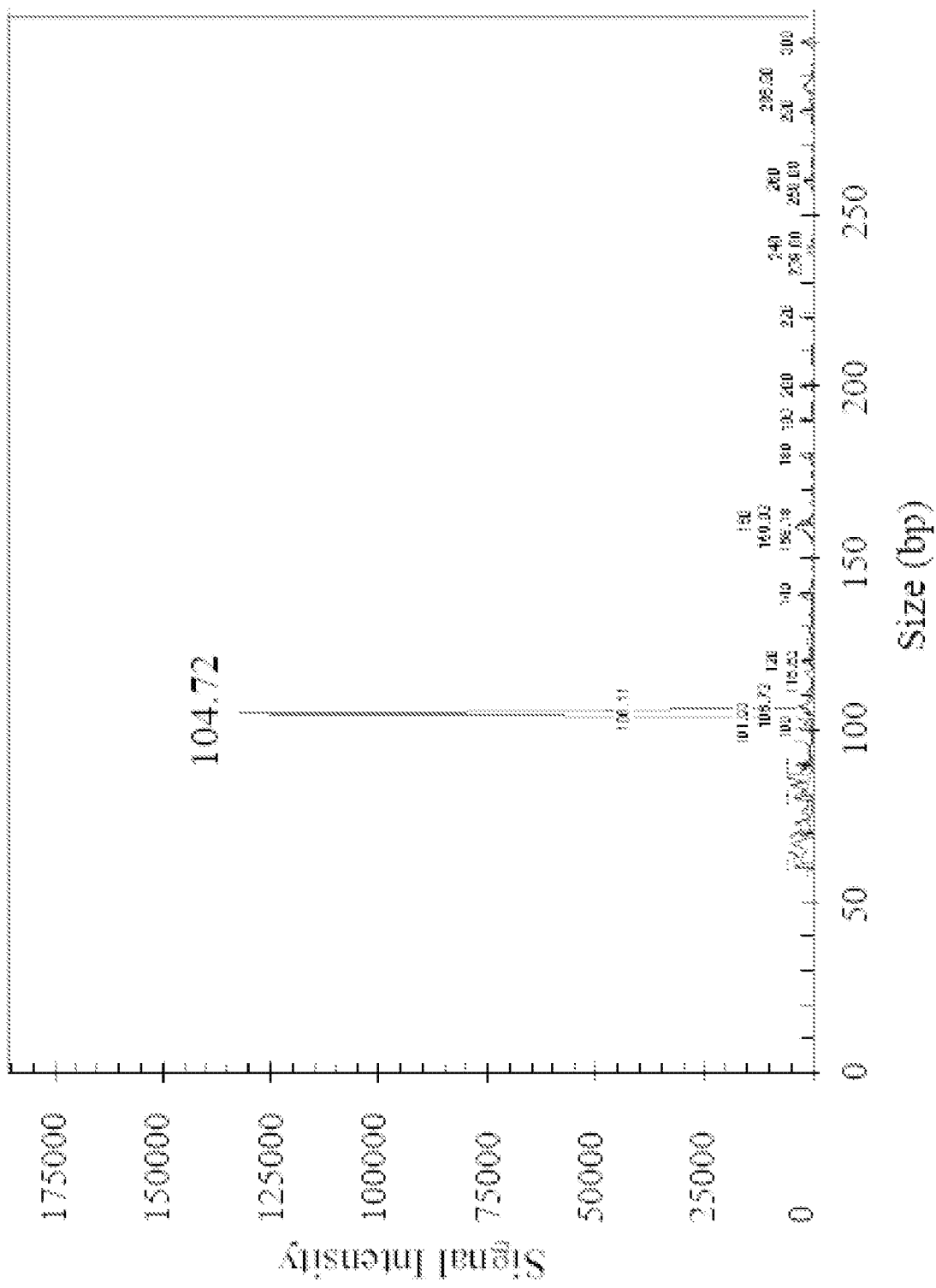
Figure 18:
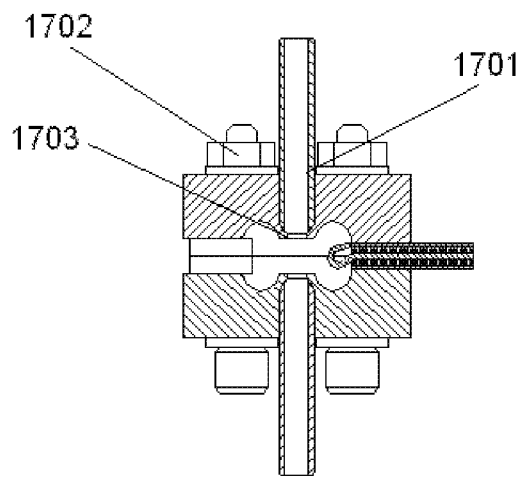
Figure 19:
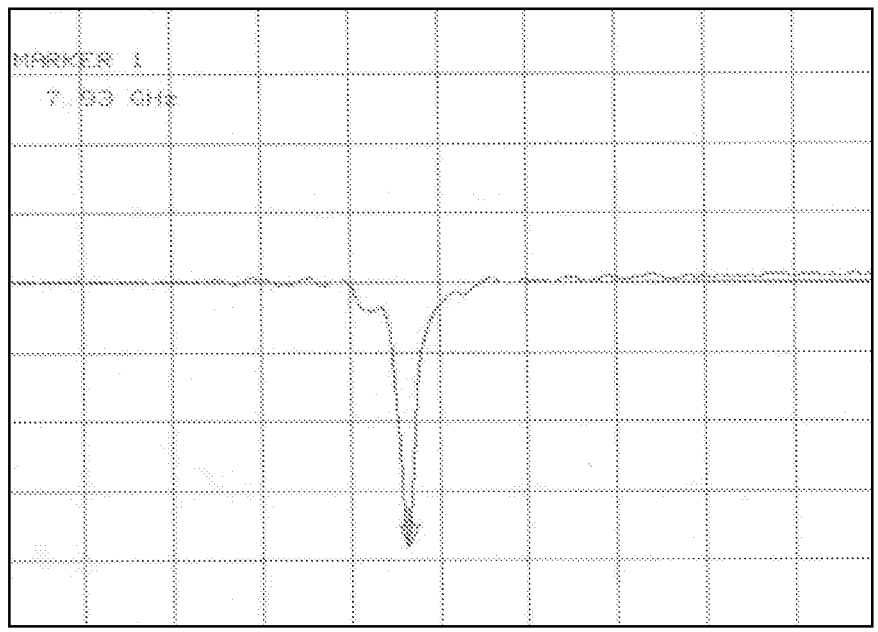
Figure 20:
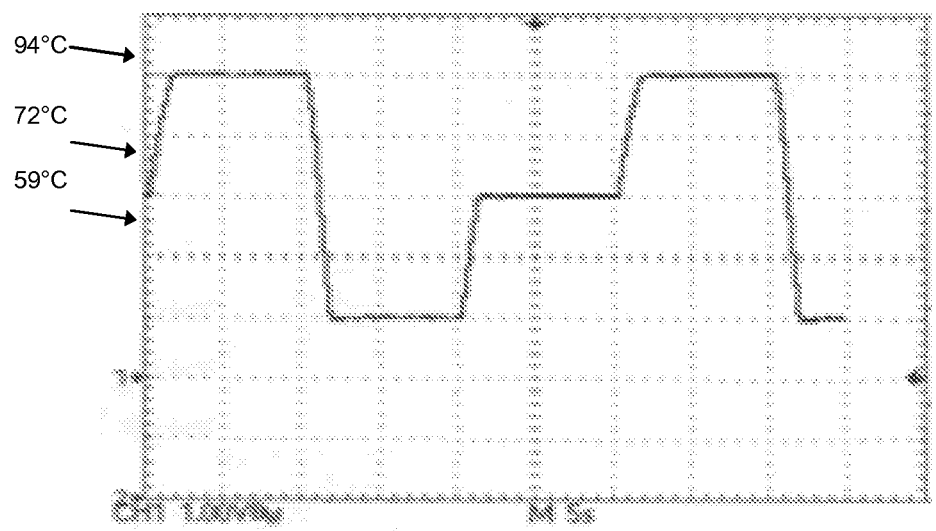

FIG. 8a shows a UV transilluminator image of PCR products obtained in stability testing of gel concentration; and FIG. 8b shows a UV transilluminator image of PCR products obtained from stability testing of gel of 4 weeks stored at 4° C. by way of methodology of the present invention;

FIG. 9 shows a visualisation of the electro-kinetic movement resulting from the applied voltages associated with the geometries seen in Table 2, in which A and B visualise the two most effective geometries respectively and according to the methodology of the present invention;

FIG. 10 is a schematic illustration of a microfluidic device according to the present invention, and for the electro-kinetic injection of a sample from an agarose gel filled T section into a capillary electrophoresis separation channel filled with polyethylene oxide separation medium in which A-D indicates the location of platinum electrodes;

FIG. 11 shows a visualisation of an unsuccessful electro-kinetic injection in agarose gel matrix according to the methodology of the present invention;

FIG. 12a shows graphically the profile acquired from an EK injection in TE solution according to the methodology of the present invention; and FIG. 12b shows graphically the profile acquired from an EK injection in 1.5% agarose gel according to the methodology of the present invention;

FIG. 13 shows graphically an example of a profile acquired from an optimized EK injection in 1.5% agarose gel according to the methodology of the present invention;

FIG. 14 shows a visualisation of a successful electro-kinetic injection in agarose gel matrix with (a) and without (b) a bubble present according to the methodology of the present invention and for which operating voltages and times are given in Table 1;

FIG. 15 shows a schematic view of a microfluidic device showing integrated DNA extraction and amplification chambers and location of electrodes for electro-osmotic pumping;

FIG. 16 shows graphically the amount of DNA recovered from the monolith during the elution step compared with the amount of DNA initially added into the device of FIG. 15;

FIG. 17a shows a visualisation of the agarose gel showing the PCR products generated by the system of FIG. 15;

FIG. 17b shows graphically the Amelogenin PCR product, generated by the system of FIG. 15, analysed by capillary electrophoresis for accurate sizing;

FIG. 18 is a section through a microwave heater suitable for applying thermal cycling to a microfluidic device according to the present invention;

FIG. 19 is a graphical output from a network analyser displaying a drop in reflective power indicating the exact resonant frequency of the microfluidic device for determining operational parameters for the heater of FIG. 18; and FIG. 20 is a thermal cycle obtained for the heater of FIG. 18.

There is provided a microfluidic sample processing device having micro-channels. The micro-channels are etched into a substrate which is preferably glass but could also be plastic or other suitable substance. The substrate measures in the region of 120 mm by 60 mm or can be of other suitable size dictated by the application or system in which it is to be used. The substrate may additionally comprise gel based separation media and reagents within its micro-channels; and electrical contacts as necessarily required for it to be coupled to a power source and/or function within a DNA analyser system. The gel based separation media and reagents are preloaded into the micro-channels of the device by way of hydrodynamic pumping, to control the injection hydrostatically, for example by suction or pressure. The glass substrate is then sealed by a lid bonded thereto to enclose the internal micro-channels defined therein. Other means of attaching the lid can also be suitable and attachment of the lid by means other than bonding is not excluded.

The preferred substrate material for the microfluidic device is glass as glass technology is already well established and has been well characterised with respect to its chemical response to most reactions.

Figure 3:
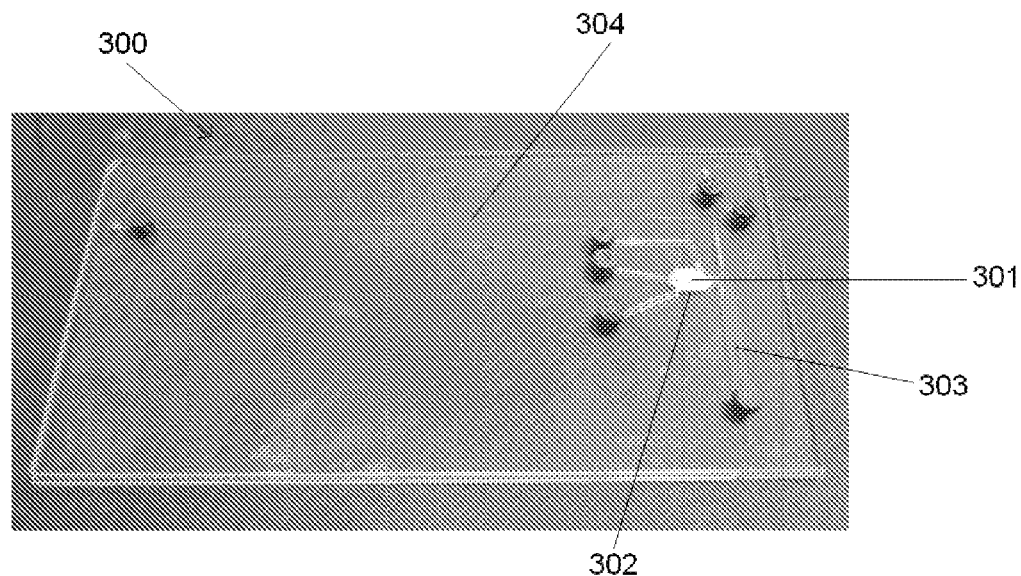
FIG. 3 shows the key parts of a microfluidic device according to the present invention.
Figure 4:
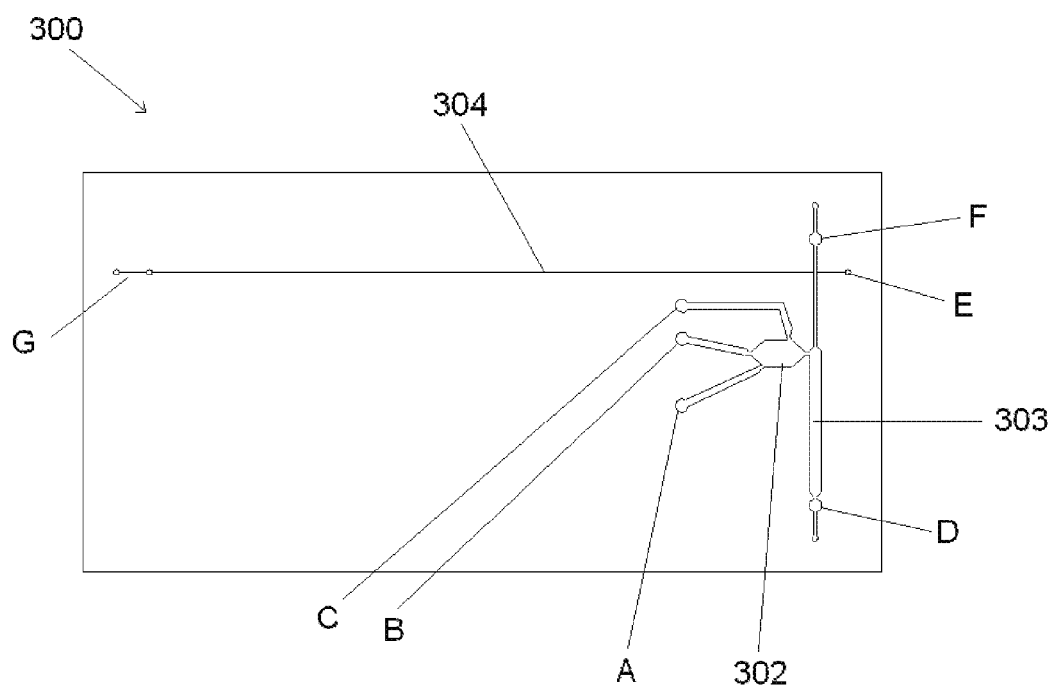
FIG. 4 shows a schematic view of a microfluidic device according to the present invention.

The microfluidic device (300) comprises three main components, namely, a DNA extraction chamber (302), a PCR chamber (303) and separation and detection channel (304) all of which can be seen in FIGS. 3 and 4 and all of which are in fluidic connection/cooperation with each other.

As mentioned previously, unlike the prior art, the microfluidic device (300) of the present invention requires no external pumping during use in, for example, a DNA analyser system. Instead a plurality of electrodes are used to electro-kinetically manipulate fluid by electroosmotic flow or electrophoresis either to instigate bulk flow or discrete movement of charged chemical species within the gel based reagent structure within the micro-channels. The present application shows the use of seven electrodes but more or fewer is also possible.

The microfluidic device (300) of the present invention is specifically designed to make its manufacture inexpensive by keeping all the hardware requirements external to the microfluidic device. This allows for the microfluidic device to remain economical and thus ideal for single use analysis which is of course particularly advantageous in the field of forensics or crime scene investigation where the used microfluidic device may be required to form the basis of evidence.

In the microfluidic device (300) of the present invention, the use of gel filled channels or capillaries to support the process reagents and sample DNA has been found to provide enhanced stability with respect to electro-kinetic control of the sample DNA when compared to solution based (prior art) methodology even when bubbles are present in the system. The gel may be in the form of a matrix but, in whatever form it is present, it should be capable of fixing the different process reagents with precision localisation in the microfluidic device over prolonged periods.

Before a microfluidic device (300) comprising microchannels can be used it has to be prepared as outlined in detail below, with particular reference to the schematic view of the microfluidic device of FIG. 4:

Microfluidic Device Preparation

Monolith preparation: A silica based extraction monolith is formed in a hexagonal extraction chamber (302) of the microfluidic device (300) by a pressure injection of a solution of 10:1 ratio of potassium silicate and formamide into the sample introduction port (301). The surrounding channels are filled with 3% glycerol hydroxyl-ethyl cellulose (HEC) gel, ensuring the silica solution remains in the hexagonal extraction chamber (302) during curing of 95° C. for 12 hours. The HEC gel is washed from the channels using water following the curing process. The silica based monolith is manufactured with potassium silicate (9% $K_2O$, 21% $SiO_2$) and formamide (98%).

Preparation of channel A: An agarose wash delivery gel is made by dissolving low melting point agarose gel in deionised water to give a concentration of 3% (w/v) (0.0030 g agarose in 100 µl deionised water) and heated to 75° C. When the gel has formed but whilst still in molten form, an 80% ethanol and 20% 1M sodium chloride solution is added, mixed and pressure injected into port A to fill the channel length from the inlet at port A to the monolith positioned in the extraction chamber (302).

Preparation of channel B: Low melting point agarose is dissolved in DNA/RNA free water, and heated to 75° C. for 10 min, the concentration of the gel is kept low so a high capacity of water is free to move through the gel. When the gel has formed but whilst still in molten form the gel is pressure injected into port B to fill the channel length from the inlet at port B to the monolith positioned in the extraction chamber (302).

Preparation of channel C: Low melting point agarose is dissolved in DNA/RNA free water and heated to 75° C. for 10 min. Whilst still in molten form the gel is pressure injected into port C.

Preparation of the separation channel (304): Polyethylene oxide (PEO) gel is made up to a concentration of 2.5% in 1× Tris-EDTA buffer by a prolonged stirring method; it is then introduced into the device via pressure injection into port G. The viscosity of the gel enables control of the flow to be achieved such that the injection is carried out only to the intersection of channel D-F. In an alternative embodiment, other gels having suitable viscosities may be employed in the separation channel such as linear polyacrylamide (LPA) gel with 6 M urea in 1× Tris TAPS EDTA (TTE) buffer.

Preparation of the PCR chamber (303): Low melting point agarose is dissolved in DNA/RNA free water, and heated to 75° C. for 10 min. When the gel has formed and whilst still in molten form the PCR reagents are added ($NH_4$ buffer, BSA, forward and reverse primers, dNTPs, $MgCl_2$ and Taq polymerase) and mixed. The "PCR gel" is injected into the PCR chamber (303) whilst still in molten form via pressure injection into port D, filling the channel D-F and to port E.

The ports A-G are then closed with a conductive polymer plug which is connected to electrodes and powered by a power source which may be located in a first component of the integrated analyser system.

The stages of the entire analytical method (at least post-cell lysis) take place within the sealed microfluidic device (300) of the type described above. Prior to use in the analyser system, the microfluidic device (300) has to be preloaded with reagents having the appropriate chemistry for each of the required stages and the device is preferably stored at 4° C. In one mode of operation, a lysed sample may be subsequently manually loaded thereon once the user is "on site". In another mode of operation, lysis of a sample may also take place on or at the device. These alternatives are discussed in more detail below.

Figure 5:
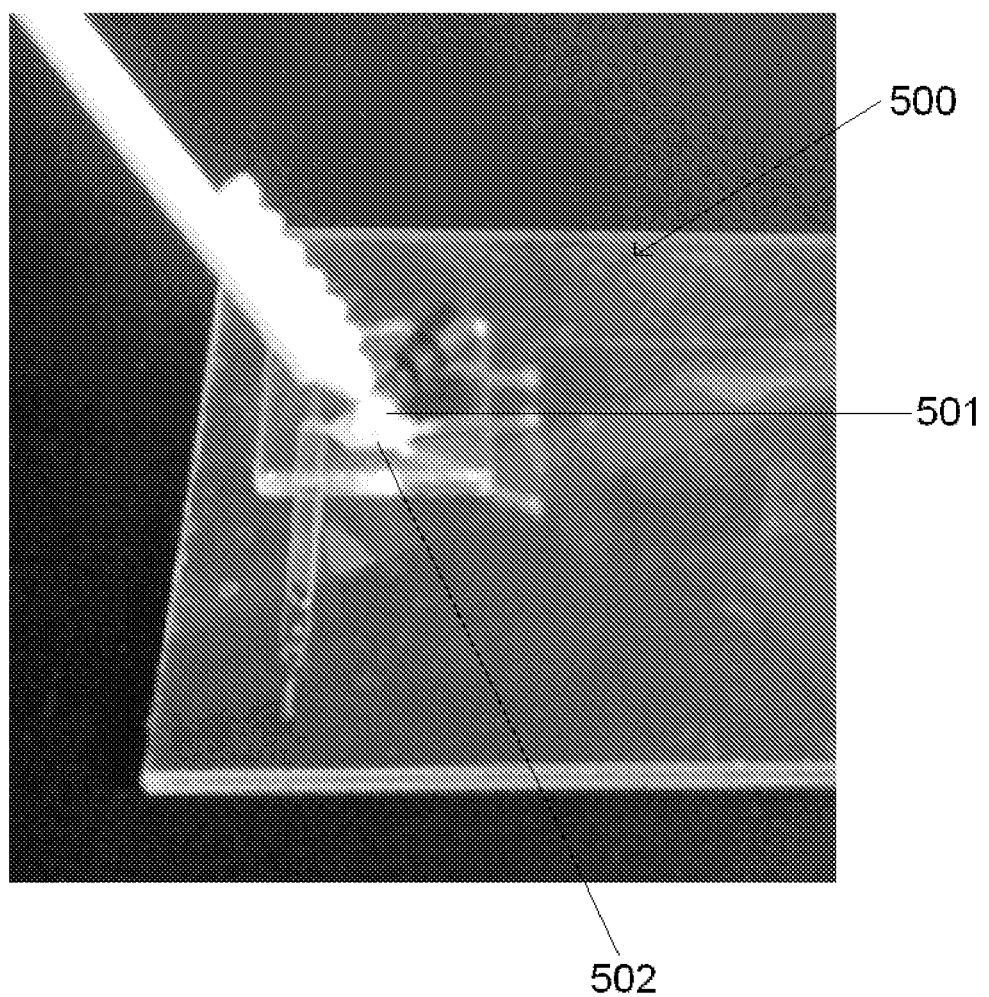
FIG. 5 shows a microfluidic device according to a second embodiment of the invention comprising an alternative sample introduction device.

Controlling the injection of a lysed sample and DNA into capillary channels is very important to obtaining reproducible separations and reliable detection resolution. Injections into a microfluidic device can be controlled either hydrostatically, by suction, pressure or gravity, or electro-kinetically which intrinsically lends itself to more precise and accurate control of sample introduction over hydrodynamic systems, whilst at the same time removing the need for external pumps, actuators, valves, etc. In this embodiment, loading of the sample is carried out via the sample introduction port (301), for example by pipetting a few microliters of lysed sample into the sample introduction port (301) or by applying the sample to a lysis agent soaked sponge (501) and applying or holding the sponge (501) to the sample introduction port (as illustrated in FIG. 5). From there the sample soaks into the silica porous monolith in the DNA extraction chamber (502). The introduction port is then sealed with a cap and the sample is manipulated within the chambers and channels by applying electric fields to electrodes positioned at A-G and as shown in FIG. 4.

Figure 1:
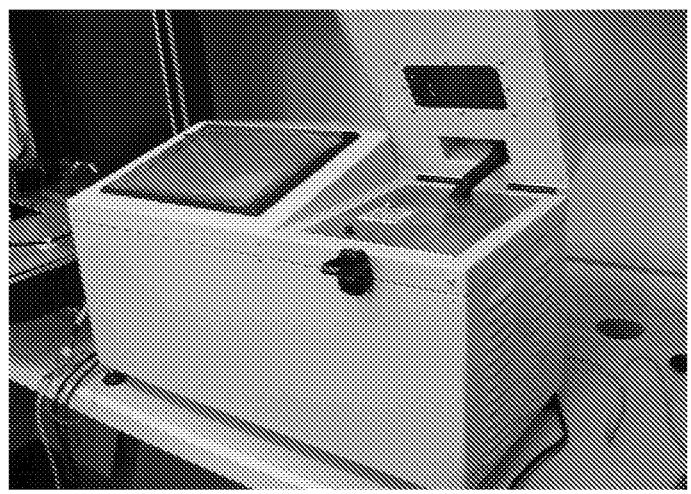
FIG. 1 shows the containment means of the system of the present invention containing the first component i.e. the hardware.
Figure 2:
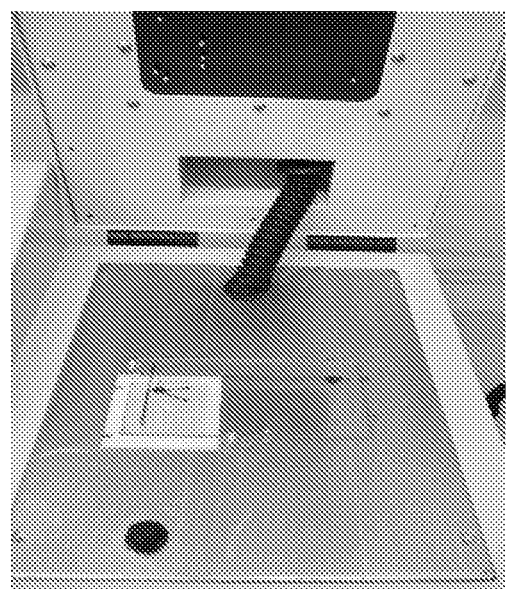
FIG. 2 shows the containment means of the system of the present invention with the microfluidic device in situ.

The system itself comprises a fully integrated, portable DNA analyser system which comprises containment means (as illustrated in FIGS. 1 and 2) having two distinct but cooperating components. The first component is a control unit, which contains all the necessary hardware and software to control processes such as heat cycling and detection. The second or further component is the microfluidic device which contains the sample and related processing reagents.

The entire analytical method post cell lysis takes place within the sealed microfluidic device (300) of the type described above. In the preferred case cell lysis is carried out in a sponge (501) loaded with lysis agent, and this stage may also take place on the device (500). The first component of the containment means which comprises all the hardware for controlling sample movement, PCR amplification and analysis is external to the microfluidic device (300, 500). The containment means of the system comprising the first component, i.e. the hardware can be seen in FIG. 1 and the microfluidic device can be seen in situ within the containment means of the system in FIG. 2.

The analyser system of the present invention is controlled via a touch screen control panel and is fully automated such that once the lid is closed the analytical process will run to completion producing the required DNA profile. The microfluidic device (300, 500) once loaded with the sample/lysed sample is placed within the system and an electrical bias is put between electrodes A and C to wash the DNA from the lysed sample with the alcohol solution as described in the preparation of channel A above to remove cell debris and other material which could potentially interfere with the process, such as heme molecules present in blood samples. Then a bias is placed between ports B and D which pumps water from channel B across the silica monolith in the extraction chamber (302, 502) of the device (300, 500), thereby eluting the DNA into the gel filled PCR chamber (303). There it is cycled around 25 to 30 times through three PCR temperatures in the presence of known suitable reagents to amplify fragments of the DNA required for DNA profiling. These reagents may also contain fluorescent dyes that can attach to selected DNA fragments so they can be detected during the separation process. The amplified fragments (for example, the PCR product from the amplification of the eleven loci used for standard DNA fingerprinting) are then drawn electro-kinetically to the neck of the separation channel (304) where a small defined quantity is introduced to the separation channel (304). This is also done using electrical fields in which a large electrical bias is applied to the separation channel (304), at electrodes G and E, such that the DNA fragments of the amplified product separate as they move down it.

The electrode contacts are generally in the form of having a diameter of approximately 500 µm, and platinum wire is preferred. More preferably, a conducting polymer, for example carbon filled polystyrene is used as electrode contacts for the device and gold-coated copper electrodes are used to connect the control unit power supplies to the polymer electrodes.

The separation of the DNA fragments of the amplified product is effected by their charge and size as they pass through the gel matrix. Their migration time essentially sizes them. The process of electrophoretic separation of nucleic acid fragments based on size is a well known technique and need not be further explained here. In this embodiment of the present invention, the detection of these fragments is carried out using at least two lasers and two spectrometers. The detector is only required to know that the laser emits a very exact wavelength of light so it can be distinguished from the four frequencies of the fluorescent dyes used to mark the nucleic acid fragments. In short, the two lasers excite the fluorescent dyes (in this case four) to allow the two spectrometers or detectors (two are required to allow the system to be "blind" to the light of the 2 lasers but still see the four fluorescent dyes) to identify when the fragments pass the detection window close to port thereby enabling the DNA profile or fingerprint to be compiled. The machine, upon completion of the run, outputs the profile in graphical form similar to commercial sequences typically manufactured by ABI (Applied Biosystems Ltd, Warrington, United Kingdom).

A method for using a microfluidic device in an analyser system is also provided and described in greater detail below. Essentially a lysed sample to be tested is manually introduced into the microfluidic device or the sample to be tested is introduced onto a sponge loaded with a lysis agent for lysis thereof on the device. The lysed sample is then absorbed onto a silica monolith and DNA then extracted in situ on the silica monolith and washed before being eluted and amplified using the PCR method after which, fluorescently labelled segments of DNA are separated to yield a genetic fingerprint. The output of the system is compatible with the DNA database held within the UK national Forensics Science Service, but can easily be structured to be compatible with those of other countries if required.

The method of using a microfluidic device of the present invention in an analyser system is described below in more detail with reference again to FIG. 4:

a) 10-50 micro liters of sample lysate and guanidine hydrochloride is manually loaded onto the silica monolith located within the DNA extraction chamber (302) of the microfluidic device (300) using the sample introduction port (301).

b) Using electrodes located at ports A and C of the microfluidic device (300), the lysed sample containing the DNA is washed by moving 80% ethanol solution from the wash inlet (port A) across the DNA extraction chamber (302) containing the silica based extraction monolith to the wash outlet (port C). This is achieved by applying a bias across the ports and instigating electro osmotic flow (EOF). Typical voltages to instigate EOF are 50-150 v/cm (see Table 1). The 80% ethanol solution washes the monolith of cell debris and unwanted matrix to enable recovery of the DNA contained within the lysed sample.

c) The DNA remaining on the silica monolith is then eluted into the PCR chamber (303) using $H_2O$ by applying a bias between ports B and D of the microfluidic device (300) thereby instigating EOF flow (see Table 1).

d) The DNA is amplified to form DNA fragments using the polymerase chain reaction (PCR). The PCR chamber (303) is heated cyclically through 3 discrete temperatures; as a result the selected DNA fragments are amplified exponentially. Suitable probes are used to provide amplified fragments of interest. On completion of between 25 to 30 cycles of the PCR process, the gel containing the amplified product is allowed to solidify, i.e. return to ambient temperature.

e) The PCR product containing the DNA fragments is electrophoretically moved from the PCR chamber (303) to the neck of the separation channel (304), where it is electro-kinetically injected into the separation channel (304) of the microfluidic device (303) using a pinched injection technique, which is well-known in the art. In this way, a small fraction of the PCR product containing the DNA fragments is pulled into the separation channel (304) for controlled time (see Table 1) and then voltages are applied to electrodes D, E and F to pull back the PCR product not injected into the separation channel (304), thereby forming a discrete slug of the injected PCR product. Voltages are then applied to electrodes D, E, F and G (as detailed in Table 1) to focus the charged DNA fragments of the discrete slug of the PCR product prior to separation beginning.

f) The DNA fragments of the injected PCR product is electrophoretically separated along the separation channel (304) of the microfluidic device (300) by applying a bias between ports D-G (see Table 1).

TABLE 1 the applied voltage and times used for reagent and DNA fragment mobility.

| STEP | Approx. voltage applied at each electrode | | | | | | | Approx. Time |
| --- | --- | --- | --- | --- | --- | --- | --- | --- |
| | A | B | C | D | E | F | G | |
| b) DNA clean up | 1000 V | — | 1 V | — | — | — | — | 180 s |
| c) DNA elution | — | 1000 V | — | 1 V | — | — | — | 300 s |

TABLE 1-continued the applied voltage and times used for reagent and DNA fragment mobility.

| STEP | Approx. voltage applied at each electrode | | | | | | | Approx. Time |
|---|---|---|---|---|---|---|---|---|
| | A | B | C | D | E | F | G | |
| d) PCR movement | — | — | — | 1 V | — | 1000 V | — | 180 s |
| e) PCR product injection | — | — | — | 500 V | 1 V | 100 V | 1000 V | 30 s |
| | — | — | — | 2000 V | 1 V | 400 V | 500 V | 30 s |
| | — | — | — | 3000 V | 1 V | 600 V | 700 V | 60 s |
| f) Separation | — | — | — | 2000 V | 1 V | 400 V | 4000 V | 900 s |

The electric potentials in the above example were generated using a 4×0-1000 V D.C power supply unit although other suitable power supply can be used. Additionally, when a high voltage above 1000V was required a 10 kV power supply was used. Both the power supplies are accurately controlled using suitable software.

The invention will be further described by way of the examples below with reference to the drawings. These examples show the re-optimised operating conditions for the individual processes (DNA extraction, amplification and separation and detection) taking place on the integrated microfluidic device of the present invention, which were compromised as a result of integration. By appreciating the interactions between the different parts of the device, the inventors have understood the effect that integration has on each of these processes. Accordingly, the conditions set out below represent those compromised operating conditions for extraction, amplification and separation and detection which can effectively be employed in an integrated microfluidic device of the present invention.

EXAMPLE 1

DNA Retrieval and Loading

In an example of the use of the invention, a biological sample containing DNA was extracted from buccal cells collected from the cheek of a volunteer.

In a first alternative of the example, the biological sample was collected from buccal tissue using QIAamp® DNA Micro Kit extraction kit or similar. The quantity of the sample extracted was determined using a POLARStar OPTIMA plate reader to similar type, and then diluted to create a standard concentration of 5 ng/µl.

A silica based monolith was prepared by activating its silica surface with 1×TE buffer. 5 µl of the sample standard solution was mixed with 120 µl of guanidine hydrochloride and loaded on to the monolith by hydrodynamic pumping using a flow rate of 5 µl/min.

In a second alternative of the example, buccal cells were collected from an individual by scraping a sterile swab along the inside of the cheek, to be used as the biological sample. The microfluidic device was provided with a 3 mm top plate with a 3 mm hole above the DNA extraction chamber (502) to act as the inlet for the biological sample. This inlet was filled with a porous sponge (501) soaked in guanidine hydrochloride solution. Buccal cells were transferred from the swab to the sponge (501) via a manual interface.

The guanidine hydrochloride solution serves to lyse the buccal cells, releasing DNA, and subsequently facilitates its binding to the DNA extraction monolith. The swab is then removed and a dual function plug is used to seal the microfluidic device (500) preventing sample loss/contamination. In addition, the plug applies pressure to the sponge (501), resulting in transfer of the lysed sample-guanidine hydrochloride solution over the monolith and into the waste channel. The DNA remains bound to the monolith, ready for the washing and elution steps required to complete the DNA extraction process.

Waste Removal

Any cellular debris still present in the monolith pores were washed away using an 80% ethanol wash (% v/v). The agarose wash delivery gel (in channel A) was made up to a concentration of 3% (0.0030 g agarose in 100 µl DNA/RNA water) and heated to 75° C., once the gel was formed and whilst still in molten form 100 µl of 80% ethanol and 20% 1M sodium chloride solution were added, the gel was then reformed on cooling thus capturing the ethanol solution inside. The ethanol gel was introduced into the wash channel A whilst still molten such that it interfaced with the silica monolith. Platinum electrodes at points A and C were then secured into place and a field strength of 100 Vcm$^{-1}$ applied for 5 minutes to wash away any cellular debris from the silica monolith. A comparison of field strengths was performed to establish the optimum field strength to establish EOF movement of 80% ethanol and 20% 1M sodium chloride solution in both gel and free solution see for example Table 2.

EXAMPLE 2

Preparation of PCR Gel

The PCR gel was prepared by dissolving low melting point agarose gel in DNA/RNA free distilled water and heating to 75° C. for 10 minutes. Once the gel was formed and whilst still in molten form the PCR reagents were added (2 µl of 10×NH$_4$ buffer, 2 µl of BSA, 2 µl of forward primer, 2 µl of reverse primer, 1 µl of dNTPs, 0.4 µl of MgCl and 0.4 µl of Taq polymerase) and mixed, on cooling the gel retained the reagents. Electrodes B and D were secured into place and an electric potential of 100 Vcm$^{-1}$ applied for 5 min, the experiment was performed on an ice block to maintain the integrity of the PCR reagents. Once the electro-kinetic movement was complete, the PCR gel was removed from the channel by pressure injection and collected. The resulting solution was then amplified in a thermal cycler, separated by slab gel electrophoresis and observed via the UV transilluminator.

The concentration of the gel and reagents was investigated to determine the most appropriate condition to successfully facilitate the PCR amplification process, whilst still maintaining reagent stability. The short term and long term stability of the reagent gel was investigated. For example, the reagent gel was prepared as described previously and stored for controlled periods of time at room temperature and at 4° C. DNA template was added to the control samples which were then amplified exponentially in a thermalcycler.

Different electrode potentials and times were investigated in order to gauge the flexibility of the system, the different electrode applied voltage combinations are detailed in Table 2.

TABLE 2 illustrates the different combinations applied to electric fields the electrodes.

| | Electrode A | Electrode B | Electrode C | Electrode D | Time |
|---|---|---|---|---|---|
| Sequence 1 | 50 Vcm$^{-1}$ | 50 Vcm$^{-1}$ | Ground | — | 5 mins |
| Sequence 2 | 100 Vcm$^{-1}$ | 100 Vcm$^{-1}$ | Ground | — | 10 mins |
| Sequence 3 | 50 Vcm$^{-1}$ | 50 Vcm$^{-1}$ | Ground | — | 5 mins |
| | Ground | Ground | 50 Vcm$^{-1}$ | — | 20 secs |
| Sequence 4 | 100 Vcm$^{-1}$ | 100 Vcm$^{-1}$ | Ground | — | 5 mins |
| | Ground | Ground | 100 Vcm$^{-1}$ | — | 20 secs |
| Sequence 5 | 100 Vcm$^{-1}$ | — | Ground | — | 5 mins |
| | Ground | — | 100 Vcm$^{-1}$ | — | 10 secs |
| Sequence 6 | 100 Vcm$^{-1}$ | — | Ground | — | 10 mins |
| | — | Ground | 100 Vcm$^{-1}$ | — | 10 secs |
| Sequence 7 | 100 Vcm$^{-1}$ | — | Ground | — | 5 mins |
| | — | Ground | 100 Vcm$^{-1}$ | — | 10 secs |
| Sequence 8 | 100 Vcm$^{-1}$ | — | — | Ground | 5 mins |

Results and Conclusions

Waste Removal

Figure 6:
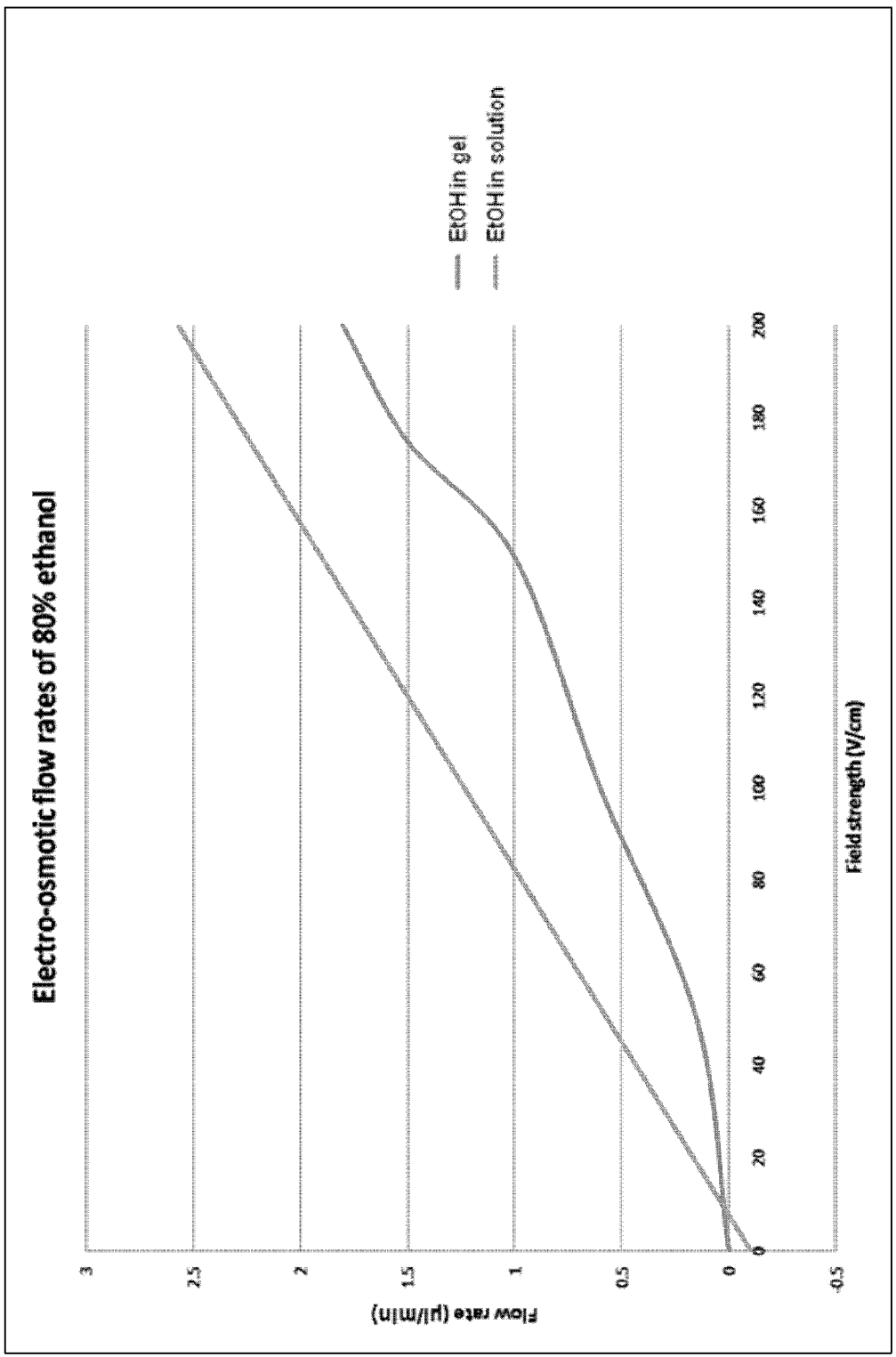
FIG. 6 is a graphic illustration of the movement of 80% ethanol wash solution (v/v) and 80% ethanol wash solution in gel (v/v) by electro-osmotic flow across a silica based monolith in a microfluidic device according to the present invention.

As iso-propanol, which is typically used for the wash step in DNA extraction clean-up did not support EOF, a solution of 80% ethanol was used. FIG. 6 illustrates the movement of 80% ethanol wash in solution (v/v) and 80% ethanol wash solution in gel (v/v) by electro-osmotic flow across a silica monolith.

As expected, the flow rate of the wash solution (FIG. 6 upper line) was more rapid than that obtained from the same solution in gel format (FIG. 6 lower line). For the gel, the relationship between field strength and flow rate is non-linear due to the interference effect of the cross polymer network on the bulk flow of liquid. However, the agarose gel solution was found to be capable of supporting electro-osmotic pumping across a monolith at an acceptable flow rate, enabling the removal of any cellular debris from the monolith. This is achieved by the mechanism described above in which the DNA of the lysed sample are absorbed on the monolith surface but cellular debris or red blood cell (which may be present in the lysed sample) are not as they are washed off the monolith by bulk movement of the ethanol solution from channels A to C. The DNA fragments are then eluted clean (in a form suitable for PCR) from the monolith using water from channel B.

EXAMPLE 3

Development of Reagent Gel

After the application of the electrical potential, the solution accumulated at each electrode was collected and the DNA quantified 65% of DNA recovered was found at the negative electrode whilst 22% was recovered from the positive electrode (at inlet port F of FIG. 4). This was likely due to a small amount of electrophoretic movement occurring when the DNA was introduced at the same port. The remaining DNA-(13%) was detected in the ethanol wash. These results support the claim that DNA can be successfully extracted from the monolith by electro-osmotic flow in the concentration required for PCR amplification.

The DNA extracted from the monolith by electro-osmotic pumping was of sufficient quantity and quality for PCR amplification to be carried out. The results also established the stability of the reagents in gel form even when a relatively high electric field was used.

A series of agarose gel concentrations were then investigated (10%, 5%, 3% 1.5%, 1% and 0.75%) to determine the ideal concentration of gel which would allow the PCR reaction to occur, whilst still maintaining the stability of the reagents for extended periods of time. Of the concentrations investigated the visualisation of the results for solutions 0.75-3% are presented in FIG. 8a, the results obtained from 5 and 10% were poor due to adverse viscosity effects of the gel and were immediately excluded from the study. From FIG. 8a it can be seen the PCR reaction was more successful in the 0.75% gel due to the stronger band present on the plate, however preliminary tests indicated that this concentration of gel provided little long term stability and protection for the reagents. The bands obtained at 1% and 1.5% gel concentration were undistinguishable from each other so it was decided to proceed with a gel concentration of 1.5% to attain a successful reaction and maintain reagent stability.

The results of the stability tests can be seen in FIG. 7 which is a UV transilluminator image of PCR products obtained through the electro-kinetic movement of DNA into PCR reagents and indicate a trend of reducing stability of the PCR reagents when not kept refrigerated. Based on stability test 1 where the gel was left for 30 minutes at room temperature, there is evidence that the PCR reaction proceeded to some degree, however some mis-priming was evident. On the other hand in stability test 2, in which the gel was left for 1 hour at room temperature FIG. 7 shows that the reagents were rendered completely unusable. The results of the second stability test can be seen in FIG. 8b, and suggest the reagent gel can be successfully stored at 4° C. for four weeks, proving the stability of the reagents is greatly increased when incorporated into a gel matrix.

The result obtained from the investigation of the different applied potentials (see Table 2), indicated that the system is highly flexible and thus shows great potential for transference to other applications. The results did highlight sequence 8 to be preferable to others investigated.

EXAMPLE 4

Preparation of Reagent Gel

A microfluidic device (300) as shown in for example FIG. 3 or 4 was cleaned and prepared by flushing through with 1M hydrochloric acid followed by 1M sodium hydroxide and deionised water before drying. The PEO gel was loaded into the separation channel (304) of the microfluidic device (300) by pressure injection into port G.

Agarose gel was then prepared by dissolving 0.0029 g of low melting point agarose in 100 µl of DNA/RNA free water, creating a gel concentration of 2.94%. The solution was then heated in a water bath at 75° C. for 10 min to allow the gel to form. While the gel was still in liquid form, 10.2 μl of the gel was added to 9.8 μl of the sample, the visualisation agent (in this case fluorescently labelled primers) was added and mixed. The final gel solution which had a concentration of 1.5%, was injected into the microfluidic device warm by pressure injection into port E in order to ensure equal filling of sample matrix into both arms of the cross bar (D-F). Finally platinum wire electrodes were pushed into the two gels as indicated in FIG. 10.

In FIG. 10, the length of the separation channel (902), from the T-section (901) to port D is 800 mm and the diameter of this channel (902) is 0.2 mm. The length of the channels at the T-section to ports A, B or C are 5 mm and the diameter of the vertical channels are 0.6 mm.

Once the microfluidic device (300) was prepared the sample and separation matrices were inspected to ensure no bubbles or debris that could cause interruption to the applied electric field had been introduced by the injection process. The voltage profile was automatically applied from a preset program entered through the LabView software. This procedure was followed for each injection experiment.

Results and Discussion
Comparison of Solution (Prior Art) and Gel Based Electro-Kinetic Injections Initially, the optimum voltage profile used for the electro-kinetic injection from solution was applied to the gel matrix, in order to establish a starting point from which to optimise the EK injection for the gel based system. Results shown in FIG. 11 indicate however that injection of a sample from the agarose gel matrix to the PEO gel was unsuccessful as no fluorescent primer was transferred from the wider sample channel into the narrower separation channel shown on the right of the pictures.

The two most probable reasons for unsuccessful injection are either that the denser separation gel physically hindered the movement of the sample, or the gel interface had a detrimental effect on the electric field strength across the channel.

However, examination of the profiles acquired for the solution and gel injections as shown in FIGS. 12a and b respectively, indicated that the profiles were in fact almost identical, the only difference being the slightly squarer nature to the profile seen for the gel system. This evidence shows that the increased density of the gel has not influenced the applied electric field as the electrical resistance of both the solution and gel systems are similar.

The observed hindrance to the sample injection is therefore more likely to be attributed to a physical resistance caused by the denser gel matrix. This would suggest that the same fundamental mechanism of movement would apply in both the gel and the solution, the only difference being that the physical influence of the gel requires higher voltages and longer periods for similar movement to occur.

Accordingly a re-optimisation of the injection in the gel system was carried out and the results are compared with those obtained for a solution system in Table 3.

TABLE 3 shows the voltages and times required for the optimised electro-kinetic injection in TE buffer solution and agarose gel.

| | Applied electric field | | | | | | | |
|---|---|---|---|---|---|---|---|---|
| | Electrode A | Electrode B | | Electrode C | | Electrode D | | Applied |
| | Potential (V) | Potential (V) | Power (W) | Potential (V) | Power (W) | Potential (V) | Power (W) | Time (secs) |
| Solution based EK injection | 1 | 400 | 0.0275 | 400 | 0.0307 | 100 | 0.0747 | 5 |
| | 1 | 500 | 0.0433 | 500 | 0.0489 | 112.5 | 0.0923 | 10 |
| | 1 | 600 | 0.0557 | 600 | 0.0665 | 112.5 | 0.0889 | 10 |
| | 1 | 400 | 0.0207 | 400 | 0.0243 | 112.5 | 0.0921 | 5 |
| Gel based EK injection | 1 | 600 | 0.0587 | 600 | 0.0622 | 100 | 0.0701 | 5 |
| | 1 | 900 | 0.1398 | 900 | 0.1568 | 75 | 0.0317 | 10 |
| | 1 | 900 | 0.1338 | 900 | 0.1464 | 112.5 | 0.0830 | 30 |
| | 1 | 800 | 0.1034 | 800 | 0.1141 | 112.5 | 0.0849 | 5 |

As predicted there was a considerable increase in the power consumption required when the injection was performed in a gel or gel matrix. This increase in power can be explained from Equation 1 below which describes electrophoretic mobility ($\mu_{ep}$) (Where q is the net charge, f is the translational friction coefficient, v is the migration velocity of the component and E is the electric field) and the Hückel equation (Equation 2), which is a modified electrophoretic mobility equation, that takes into account electrophoretic movement of a species in a polymer solution ($\mu_o$), (Where η is the solvent viscosity and q is the polyion's charge and R the polyion's radius).

$$\mu_{ep} = \frac{q}{f} = \frac{v}{E} \qquad \text{Equation 1}$$

$$\mu_o = \frac{q}{6\pi\eta R} \qquad \text{Equation 2}$$

The electrophoretic mobility is expressed in terms of charge over the translational friction coefficient; however the introduction of a polymer solution necessitates the introduction of not only the viscosity of the solvent but also the radius of the poly ions. In both equations whilst the charge could be the same the added affect of viscosity and the radius of the poly ions will alter the electrophoretic mobility within the gel considerably.

Demonstrating the Robustness of a Gel Supported Injection

When examining the profile acquired for the optimised EK injection in gel (FIG. 13) it was observed that the same square nature displayed in the previous gel injection (FIG. 12b) could be seen. In general the injections in gel showed a greater degree of stability indicated by the straight even lines of the profile compared to that of the profile acquired in solution.

Figures 14A, 14B:
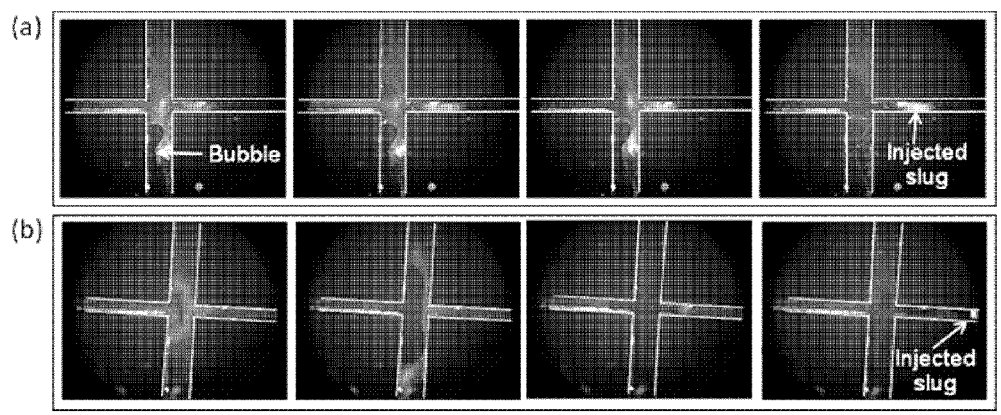

The increased stability of the gel was further displayed when an electro-kinetic injection was successfully carried out (FIG. 14b) even when a bubble was present in the system (FIG. 14a).

In the solution based system a bubble present during the electro-kinetic injection would severely compromise the fluidic movement most likely lead to failure of the process. However, in the gel system of the present invention, the presence of a bubble generates a more diffuse sample slug with a wider diameter compared to the repeated injection performed without the bubble (FIG. 14b). In addition, there is an observed concentration increase of sample developing around the area of the bubble which only dissipates in the latter stages of the injection process. However, successful injection is possible and compares well to that of the injection without the bubble deposited into the injection channel.

EXAMPLE 5

DNA Extraction, Using Carrier RNA, Integrated with Agarose Gel-Based Polymerase Chain Reaction in a Microfluidic Device Extraction of DNA from biological samples is critical for the success of downstream processes such as PCR. The use of a solid-phase extraction methodology, as discussed in this example, is advantageous as it facilitates pre-concentration of the DNA, important when limited sample material is available.

In this example, with reference to FIG. 15, all glass microfluidic devices were prepared using standard photolithographic techniques and wet-etching. Monoliths were produced in the DNA extraction chamber (1401) by thermally curing a mixture of potassium silicate and formamide. Next PCR reagents for amplification of the Amelogenin locus, including bovine serum albumin, poly(vinylpyrrolidine) and Tween-20 for dynamic passivation, were added to a molten solution of low-melting temperature agarose and injected into the PCR amplification chamber (1402) and stored at 4° C. until required.

DNA was added to 5M guanidine hydrochloride solution, with or without poly-A carrier RNA, and injected onto the monolith. Potential contaminants of downstream applications, e.g. haem protein from blood, were then removed using an EOP-based ethanol wash by applying positive potential to electrode B and a negative potential to electrode C, creating bulk electro-osmotic flow (FIG. 15). Finally, DNA was eluted into the amplification chamber by water using EOP by applying a positive potential to electrode B and a negative potential to electrode D. Once the DNA had been transferred into the pre-loaded PCR gel, thermal cycling was achieved using a Peltier heating system. PCR products were analysed off-chip using standard capillary electrophoresis.

Results and Conclusion

The use of carrier RNA led to increased DNA extraction efficiency (FIG. 16). Samples with carrier RNA (1501) (ratio 50:1, RNA:DNA) were compared to those with no carrier RNA (1503) added (n=3). The theoretical 100% recovery is shown by the 45° line (1505).

When carrier RNA is used the DNA extraction efficiency follows the ideal 100% theoretical recovery up to 25 ng of DNA added compared to only 5 ng when no carrier RNA is added to the system. At higher quantities of DNA, the presence of carrier RNA continues to give higher yields of DNA during the elution step. The use of agarose gel to encapsulate the PCR reagents has no adverse effects on DNA amplification but offers the advantage of long-term storage of the reagents on the microfluidic device at 4° C. for at least 8 weeks. Examples of the PCR products generated using this system are shown in FIGS. 17a and 17b. FIG. 17a shows a DNA size ladder (lane 1), a positive control (lane 2), a negative control (lane 3) and the PCR product from gel-based amplification in the microfluidic device (lane 4).

The addition of carrier RNA to the DNA binding solution increases the DNA extraction efficiency of thermally activated silica monoliths. The use of agarose gel to encapsulate the PCR reagents allows them to be stored on the microfluidic device. This, along with the use of EOP rather than hydrodynamic pumping, offers considerable advantages for portable applications and reduced potential for contamination.

Alternative Heater

Although the above discussion suggests, and the system is compatible with, a thermal cycler of conventional design such a Peltier heating/cooling element, an alternative that is particularly effective for rapid thermal cycling in a system in accordance with the invention is a microwave heater. An example is illustrated in FIG. 18.

The resonant cavity (1702) used to heat the sample was operated at microwave frequencies, but the heating process is not conventional microwave heating; in conventional microwave heating the dimensions of the target generally exceed the wavelength of the cavity (1702). At 8 GHz the wavelength is 37.5 mm in air and thus around 16 mm in glass; the dimension of the sample along the relevant axis is just 2 mm. Thus the heating mechanism is just radio frequency (RF) dielectric heating of the glass between the re-entrant posts of the cavity; the resonant mode of the cavity is best understood from a low frequency standpoint.

A conducting cylindrical bar (1701) bent into the form of the letter C will have a resonant frequency: the ends of the bar thus facing each other form a capacitor, and the length of the bar is a single turn coil, an inductor, in series with that capacitor. The structure is therefore able to resonate in a very simple mode—alternating current travels to and fro along the length of the bar. But it would be difficult to couple power into such a resonator and troublesome levels of power may be radiated from it.

To topologically develop the resonant bar (1701) into a shielded resonant structure it is only necessary to create a solid by rotating it 360° about the axis of the capacitor. The resulting structure is a re-entrant quasi-toroidal cavity, from which there is no radiation. The capacitance value is unchanged, but the inductance is considerably decreased—it now resembles several single turn inductors in parallel. The resonant mode, and there is only one, has its RF electric field parallel to the axis of the capacitor between the opposing centre posts. Because the posts are close together and the glass of the sample finger has a dielectric constant of around 6 there is little electric field anywhere else. The RF magnetic field runs in the direction of the toroidal cavity space around the posts and is easily excited by a magnetic loop, in our case manufactured from 2.2 mm diameter 50Ω semi-rigid coaxial cable.

The cavity (1702) was constructed from identical halves (see FIG. 18). The re-entrant posts were drilled axially to 1.6 mm diameter to admit the cooling air from an air cooling supply (1703) which impinged straight on the sample finger. A rectangular slot to admit the sample finger was machined in the side of the cavity opposite the coupling loop.

This behaves as a below cut-off dielectric-filled waveguide, the attenuation of which is given by:

$$\alpha = 8.69\sqrt{\left(\frac{2\pi}{\lambda c}\right)^2 - \varepsilon\left(\frac{2\pi}{\lambda}\right)^2} \text{ dB/unit}$$

where $\lambda c$ is the cut-off frequency and $\in$ is the dielectric constant of the glass. The attenuation for the present cavity design is thus over 20 dB, which could be increased by increasing the outer diameter of the cavity, but this was not found to be necessary. The resonant wavelength of a re-entrant cylindrical cavity is given by:

$$\lambda_0 = 2\pi\sqrt{\frac{z_0 \rho_1}{2\delta}\ln\frac{\rho_2}{\rho_1}}$$

where $\rho_1$ and $\rho_2$ are the post and cavity radii and $z_0$ its length. The presence of the sample finger decreases the resonant frequency by a factor $\in^{1/2}$. Because $z_0$ is short and because there are intrusions by the sample finger and the coupling loop into the cavity the calculation is approximate; it was tuned to 8 GHz by incremental machining.

The microwave power source was a GHz 20 W travelling wave tube amplifier used at a power levels up to 5 W and driven by a microwave signal generator. After inserting a sample finger into the cavity (1702) the resonant frequency was determined at low power by observing the resonance dip in the reflected power signal. The frequency was then noted and transferred to the signal generator. Coupling into the cavity (1702) was adjusted for a minimum of 10 dB return loss by varying the insertion depth of the coupling loop.

A control system was developed which allowed real-time adjustment of the thermal cycling temperatures during the DNA amplification process. Dwell times at the three process temperatures (DNA denaturation, primer annealing and DNA extension) are adjustable from 1 to 99 seconds, and at the initial DNA denaturation and final extension temperatures from 1 to 999 seconds.

When each microfluidic device is placed into the microwave cavity (1702) the exact resonance is obtained using a network analyser. By monitoring the reflective power the correct frequency is obtained when there is a drop in the reflected power by 10 dB. This is illustrated in FIG. 19. Tuning of the cavity (1702) is achieved by tightening the connection between the two halves of the microwave cavity (1702). The frequency is then transferred to the signal generator, ensuring microwaves are generated at the optimum frequency for the microfluidic device in question.

By using highly controlled microwave heating and air cooling the system showed limited over-shooting or under-shooting at any of the three set temperatures. Once the microwave system reached the desired temperature the variation was only ±0.1° C. which makes the system very accurate. The ramp rates for heating and cooling were 65° C./second, which allows very fast transitions between temperatures. FIG. 20 is a trace from an oscilloscope showing a close-up of thermal cycling profile. The microwave system was designed so that it was capable of performing an initial denaturing step, essential when using Hot-Start Taq DNA polymerases and also ensuring complete DNA denaturation. Also a final extension step was included ensuring that complete adenylation of the PCR products could occur. Both steps were automated into the sequence and were controllable with respect to both time and temperature.

Summary

In summary the present invention provides successful optimisation and application of a monolith to gel and gel to gel electro-kinetic injection of a DNA fragments from a gel supported matrix into a polymer gel separation matrix. Evidence of an increase in control, stability and robustness for a gel supported injection over solution based introduction has been demonstrated. Additionally the present invention shows that the gel supported sample matrix, which is known to prolong the stability of reactants, improves the operation and mobility of an electro-kinetic sample injection in a microfluidic device without compromising the overall power consumption of the device.

Additionally bubble formation a microfluidic device prepared with the gel according to the present invention did not cause any of the problems normally observed in solution based systems of excess joule heating. Although bubbles did alter the pathway of the injection mechanism substantially, the current was still maintained and an injection was produced. In a solution only fluidic system if a bubble is produced, the resultant disruption would cause a break in the electric field which would severely compromise the injection process. Finally the transfer of a DNA fragments from one gel to another was found to be unaffected by the matrix to matrix interface. Therefore use of a microfluidic device having gel supported DNA fragments and reagents according to the present invention provides a number of advantages over the prior art and as outlined above.

In summary the present invention provides a unique gel based electro-kinetic microfluidic device for use in an analyser which using electro osmotic flow & electrophoresis allows the DNA fragments of a biological sample within the device to undergo all of extraction, purification, amplification, separation in one process. This is in contrast to the prior art which provide devices which are more or less "single step" devices. Additionally the fully integrated portable analyser of the present invention in use with the microfluidic device, also of the present invention, has been found to allow coordination between each step of the DNA analysis which results in faster processing. The increased speed of such an analyser compared to larger devices has been found to be particularly evident during the PCR step.

The invention claimed is:
1. An integrated gel based microfluidic sample processing device comprising:
   a substrate having a plurality of micro-channels to form at least a DNA extraction chamber in fluidic cooperation with an amplification chamber which in turn is in fluidic cooperation with a separation and detection channel, the micro-channels containing a DNA extraction material and gel based reaction reagents necessary for processing the sample; the device further comprising electrical contacts for coupling to an external power source, the electrical contacts being capable of inducing electro-kinetic manipulation of the gel based reaction reagents and DNA extracted from the sample throughout the device,
   wherein the gel based reaction reagents comprise reagents required to conduct a PCR reaction and wherein the PCR reaction reagents are supported in a gel matrix within the microfluidic device so as to localize the PCR reaction reagents while permitting the PCR reaction,
   wherein the gel matrix is provided by an agarose gel having a concentration of from 1% to 1.5%.

2. The device according to claim 1 wherein said DNA extraction material is a solid phase extraction material located in the DNA extraction chamber.

3. The device according to claim 2 wherein said solid phase extraction material is a porous silica based solid phase extraction material.

4. The device according to claim 3 wherein said silica based solid phase extraction material is a silica based monolith.

5. The device according to claim 4 wherein said silica based monolith is a thermally initiated silica-based monolith.

6. A portable, integrated system for analysis of DNA in a biological sample comprising an electro-kinetically driven system for extraction and purification, amplification, separation and analysis of DNA fragments from said sample, said system further comprising a gel based microfluidic sample processing device according to claim 1, a plurality of electrodes positioned within the microfluidic device and coupled to a power source and the plurality of electrodes being configured to electro-kinetically manipulate the gel based reaction reagents and DNA and DNA fragments around the microfluidic device, wherein the microfluidic device is adapted to receive the sample via the DNA extraction chamber; the system further comprising a heating element coupled or adjacent to the microfluidic sample processing device;
- a detector positioned to detect DNA fragments by a detectable signal; and a portable housing configured to contain the microfluidic device,
- electrokinetically driven system, the detector and the power source.

7. The system of claim 6 wherein the heating element is a non-contact heating element.

8. The system of claim 7 wherein the heating element comprises a source of microwave radiation.

9. The system of claim 8, wherein the source of microwave radiation is adapted to achieve thermal cycling of DNA fragments.

10. A method of DNA analysis comprising:
a) introducing a sample into a DNA extraction chamber of the gel based microfluidic sample processing device of claim 1 located in an analyser system;
b) performing electro-kinetic manipulation of the sample within the DNA extraction chamber to extract DNA;
c) electro-kinetically eluting the DNA in the DNA extraction chamber to an amplification chamber;
d) amplifying the DNA in the amplification chamber to form an amplification product within a gel, wherein amplification of the DNA is performed by polymerase chain reaction (PCR);
e) electro-kinetically injecting said amplification product into a separation channel;
f) performing electro-kinetic separation of said amplification product to form a DNA profile; and prior to said introduction of said sample; and
g) storing reagents required for said PCR reaction in a gel matrix within the microfluidic device so as to localize the PCR reaction reagents while permitting the PCR reaction, wherein the gel matrix is provided by an agarose gel having a concentration of from 1% to 1.5%.

11. The method according to claim 10 wherein said sample is electro-kinetically purified by moving a wash solution from a wash inlet to a wash outlet of the DNA extraction chamber.

12. The method according to claim 10 wherein said electro-kinetic manipulation of the sample within the DNA chamber is performed by means of electroosmotic manipulation of the sample.

13. The method according to claim 10 wherein the electro-kinetic separation of the amplification product is performed by electrophoretic separation.

14. The method according to claim 10 wherein the method additionally includes the step of detecting said DNA profile and transferring said detection signals to output means such that the profile can be viewed graphically.

15. The method according to claim 10 wherein said PCR amplification of the DNA comprises thermal cycling of DNA fragments using a source of microwave radiation.

* * * * *